United States Patent [19]

Katz

[11] Patent Number: 5,776,137

[45] Date of Patent: Jul. 7, 1998

[54] METHOD AND APPARATUS FOR LOCATING BONE CUTS AT THE DISTAL CONDYLAR FEMUR REGION TO RECEIVE A KNEE PROSTHESIS

[76] Inventor: Lawrence Katz, 10 Iron Latch West, Upper Saddle River, N.J. 07458

[21] Appl. No.: 455,985

[22] Filed: May 31, 1995

[51] Int. Cl.[6] ................................................ A61B 17/58
[52] U.S. Cl. ................................. 606/88; 606/87; 606/102
[58] Field of Search ............................. 606/87, 88, 102, 606/95, 96

[56] References Cited

U.S. PATENT DOCUMENTS

| | | |
|---|---|---|
| 5,234,433 | 8/1993 | Bert et al. ............... 606/102 |
| 5,364,401 | 11/1994 | Ferrante et al. ........... 606/102 |
| 5,454,816 | 10/1995 | Ashby ....................... 606/102 |
| 5,484,446 | 1/1996 | Burke et al. ............... 606/87 |
| 5,486,178 | 1/1996 | Hodge ...................... 606/102 |

Primary Examiner—Michael Buiz
Assistant Examiner—Julian W. Woo
Attorney, Agent, or Firm—Ostrolenk, Faber, Gerb & Soffen, LLP

[57] ABSTRACT

A tool mountable on an intramedullary rod projecting from the distal end of a femur, the tool carrying anterior and posterior caliper feelers for respectively engaging the anterior surface of the femoral cortex and the posterior surfaces of the condyles of the femur. The tool is adapted to be rotated with the rod to a determined angular position. The caliper feelers are supported on the tool to measure the perpendicular distance between the anterior surface of the femoral cortex and a plane inclined about an axis located in another plane tangent to the posterior surfaces of the medial and lateral condyles and at an angle correlated to the angle of rotation of the tool. A scale on the tool indicates prosthesis size on the basis of the distance measured. A distal cutting guide is mountable on the tool while still on the rod and the cutting guide has a guide slot for a cutting tool to form a planar cut at a distal end of the femur to resect a thickness of the femur based on the distance measured by the caliper feelers. Thereafter, a conventional A-P cutting guide is mounted on the rod or a pair of reference pins to enable anterior and posterior cuts to be made.

49 Claims, 18 Drawing Sheets

METHOD AND APPARATUS FOR LOCATING BONE CUTS AT THE DISTAL CONDYLAR FEMUR REGION TO RECEIVE A KNEE PROSTHESIS

FIELD OF THE INVENTION

The invention relates to methods and apparatus for locating bone cuts on the medial and lateral femoral condyles to form seating surfaces for a femoral knee prosthesis.

The invention further relates to a tool for locating said cuts.

In particular, the invention relates to such method, apparatus and tool which enable planar cuts to be made at the anterior surfaces, the posterior surfaces and the distal ends of the medial and lateral condyles of the femur to form seating surfaces to receive the femoral knee prosthesis.

BACKGROUND

Over the years, the concepts of designs for the total knee arthroplasty have evolved to the point where with few exceptions, most are quite comparable in the design of femoral, tibial and patellar prostheses.

Major discrepancies and problems encountered are caused by physician error and failure to understand the principles of more complex alignment or ligament problems to be corrected at surgery. With the more complex alignment or "routine" degenerative knee, the major differences are the ease and consistency of instrumentation for alignment and proper bone cuts allowing proper ligament balance. This allows satisfactory motion and stability post operatively.

The distal femoral cuts must be placed to provide the knee prosthesis with a proper flexion and extension gap, proper varus-valgus alignment, proper patellofemoral relationship and proper rotation. It is customary to use an intramedullary rod placed in a retrograde fashion between the medial and lateral femoral condyles just anterior to the intercondylar notch to establish a single point of reference for subsequent bone cuts. A major problem is in the instrumentation to indicate the location of the femoral cuts which relies upon the "experience" or "eyeballing" of the surgeon. Over the years, two basic instrument system designs have become popular.

In one design (anterior referencing), the total knee alignment system takes its point of reference from a centrally placed rod and careful attention is given to the patellofemoral joint by using an anteriorly placed feeler gage. The distal femoral cut is consistent with the thickness of the prosthesis.

This instrument system operates on the principle of anatomic anterior and distal femoral cuts to allow proper ligament balancing and stability in extension as well as consistent patellofemoral placement on the anterior surface. The femur is not notched, and the anterior surface of the femoral prosthesis not elevated above the anterior surface of the femur. Notching the femur may cause a decrease in strength of the distal femur. Elevation of the anterior surface of the prosthesis will cause extremely high patellofemoral pressures in a joint that seems to be prone to a high rate of post-operative failure.

By establishing the anterior femoral cut as the benchmark or datum starting point, however, the anterior referencing instruments result in the installation of a knee prosthesis which sacrifices consistent stability in flexion due to the formation of a posterior femoral condylar cut that may leave the posterior space either too wide or too narrow. This can cause instability in flexion, or restrict flexion and cause increased wear.

The second type of instrument design (posterior referencing) is based on the concept that the flexion and extension stability are more important and the patellofemoral joint is of secondary importance. This system also uses an intramedullary rod for referencing. Although I consider all three joints as "important", when a compromise must be made, the posterior referencing systems compromise the patellofemoral joint while the anterior reference systems sacrifice stability in flexion (the posterior tibial femoral joint). Both systems allegedly equally address the distal tibial-femoral space. Neither consistently addresses the distal rotation of the femoral component.

SUMMARY OF THE INVENTION

An object of the invention is to provide methods and apparatus enabling the formation of planar cuts on the medial and lateral femoral condyles for the femur to provide seating surfaces for a femoral knee prosthesis which reliably and anatomically provide:

1. Consistent distal tibio-femoral stability.

2. Consistent distal femoral rotation.

3. Consistent placement of the anterior cut flush with the anterior surface of the femoral cortex i.e. without notching or elevation.

4. Consistent placement of the posterior femoral cut such that the distal and posterior cuts are equal (when indicated) allowing for satisfactory extension and flexion stability and motion.

The method and apparatus of the invention contemplate placement of the anatomic jointline which, in extreme cases, vary up to the difference between the anterior-posterior A-P internal measurements of the size prostheses. Based on my knowledge of total knee replacement, personal experience with numerous routine total knee replacements, numerous more complicated cases consisting of knees with flexion deformities and revision surgery, a maximum of a few mm proximal displacement of the jointline is considerably less harmful than:

1. A lax flexion gap;

2. Sloping the proximal tibial cut to accommodate for an inconsistent posterior femoral condylar cut;

3. Significantly notching the femur anteriorly;

4. Raising the anterior flanges of the prosthesis and thus the patellofemoral joint;

5. Not allowing full extension;

6. Raising the joint line;

7. Tightness in flexion;

8. Malrotation; and

9. Patient pain.

In accordance with the invention, a method is provided for forming planar cuts on the medial and lateral condyles of the femur to form seating surfaces to receive a femoral knee prosthesis, comprising:

determining a prospective planar cut at the posterior of the condyles of the femur at which the distance between the anterior surface of the femoral cortex and the prospective planar cut is substantially equal to the interior dimension of a knee prosthesis to be fitted on said femur at the anterior surface and the cut planar surface, determining the thickness of the posterior lateral or medial condyle which will be resected by said prospective planar cut, cutting the distal ends of the condyles along a plane at which the maximum thickness of resection of the more prominent condyle at said distal end is substantially equal to the thickness determined to be resected at the posterior medial or lateral condyle by said prospective planar cut, and cutting the condyles along a plane substantially flush with the anterior surface of the femoral cortex, and along said prospective planar cut.

The method further contemplates loosely placing a longitudinal intramedullary rod in the femur such that an end of the rod projects from the femur, mounting a tool on the projecting end of the rod, establishing, by said tool, an angular position of said prospective planar cut along a plane rotated at an angle of between 0° and 15° with respect to a tangential plane at the posterior of the lateral and medial condyles about an axis located in said tangential plane.

In further accordance with the method, the tool is rotated with said rod through said angle and a datum or benchmark is established by the rotated rod or by pins installed in the condyles on the basis of the rotated position of the tool. A cutting guide can be mounted on said tool, to enable the distal end of the condyles to be cut along said plane. Thereafter, the tool is removed and a second A-P cutting guide is mounted on the selected benchmark i.e. the rod or the pins and the posterior and anterior cuts are made. The axis about which the plane of the prospective cut is rotated is located in said tangential plane at the posterior surfaces of the medial and lateral condyles and can be located at either of the condyles or at any location therebetween. It is a feature of the invention that the tool remains on the rod both for the measurements and for the cutting of the distal end of the femur.

The invention also contemplates that the cutting guide supports a means which enables the cutting guide to be secured to the condyles during the cutting of the distal ends of the condyles.

DETAILED DESCRIPTION OF A PREFERRED EMBODIMENT

Figure 4:
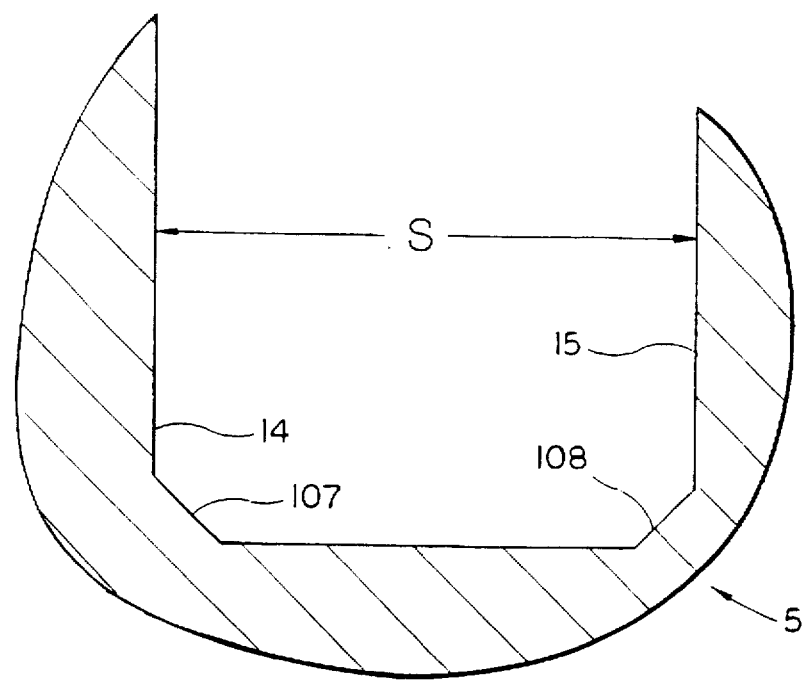
FIG. 4 is a sectional view of a femoral knee prosthesis adapted for placement on the femur after the planar cuts have been made on the femur.

The drawing diagrammatically illustrates the femur 1 and tibia 2 of a knee joint 3. The invention is concerned with the placement of planar cuts at the distal condylar region 4 of the femur 1 to receive a femoral knee prosthesis 5 (FIG. 4). The cut made on the tibia and installation of the tibial knee prosthesis is not germane to the invention except insofar that the tibial prosthesis is nominally rotated at an angle of 3° around the common axis of the tibia and femur. Accordingly, the cuts made on the femoral prosthesis must take into account this 3° rotation in order to angularly align the femoral prosthesis with the tibial prosthesis as will be explained later. The condylar region 4 of the femur is formed with a medial condyle 6 and a lateral condyle 7 separated by an intercondylar notch 8. The femur includes a shaft 9 forming the femoral cortex, the condylar region 4 being at the distal end of the shaft 9.

In order to install the femoral knee prosthesis 5 on the distal condylar region 4 of the femur 1, three planar cuts are made in the condylar region 4 to form seating surfaces for the prosthesis 5. These cuts consist of an anterior cut 10, a posterior cut 11 and a distal end cut 12. The placement of these cuts 10, 11, 12 is crucial to the installation of the prosthesis 5 and its effect on the overall function of the prosthetic knee joint.

The invention is based on complying with the following conditions.

1. Forming the planar cut 10 at the anterior surface of the femoral condylar region flush with the anterior surface 13 of the femoral cortex so as to form a continuous surface therewith free of formation of either a notch or elevation at the juncture of cut 10 and surface 13.

2. Forming the planar cut 11 at the posterior surface of the femoral condylar region at a distance D from planar cut 10 equal to the interior dimension S between the anterior and posterior mounting surfaces 14, 15 of the prosthesis 5. The dimension S is the so-called A/P distance of the prosthesis and this distance varies for different size prostheses. For example, prostheses are categorized as small, small(+), medium, large, large(+) and extra large and the A/P distance increases in proportion to the size increase.

Figure 3:
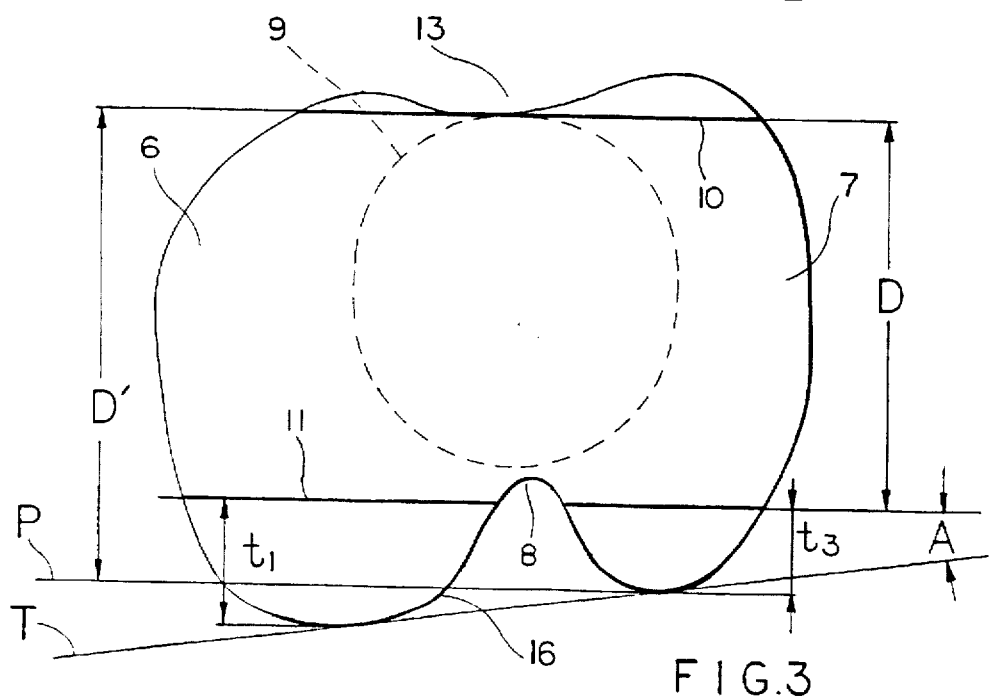
FIG. 3 is an end view from the distal end of the femur of the knee joint.

With reference to FIG. 3, therein is seen a plane T tangential to the medial and lateral condyles at the posterior surface 16 of the condylar region. The planar cut 11 is made at an angle A, with respect to plane T to angularly align the femoral prosthesis with the tibial prosthesis. Normally, the angle would be 3° to match the angle of the tibial prosthesis, however, due to anatomical conditions of the patient such as wear of the medial or lateral condyles posteriorly the angle A can vary substantially, generally between 0° and 15°. The planar cut 11 will result in resection of bone of a thickness $t_1$ at the medial condyle 6 and a thickness $t_3$ at the lateral condyle. The thickness $t_3$ is usually less than $t_1$ and controls the location of planar cut 11 so that a minimum thickness of bone is resected at the posterior surfaces of the condyles. In this regard, the thickness $t_3$ is established as the difference between distance D' between the anterior surface 13 of the femoral cortex and a plane P tangent to the posterior surface of the lateral condyle 7 and parallel to planar cut 11 and distance D between the anterior surface of the femoral cortex 13 and planar cut 11.

The thickness $t_3$ and the location of the prospective planar cut 11 therefore can be established based on measurement of the distance D and the A/P dimension of the selected size of the prosthesis. The size of the prosthesis is determined on the basis of the measurement of the distance D' and in general, the prosthesis size will be selected so that the thickness $t_3$ falls within a relatively narrow range, generally at least 6 mm and between 6 and 11 mm. The resected thickness of bone $t_1$ and $t_3$ at the medial and lateral condyles are generally unequal.

The distal end cut 12 is made so that the maximum thickness $t_2$ of bone resected at the distal end is substantially equal to $t_3$, i.e. the maximum thickness $t_2$ of bone resected at the more prominent condyle at the distal end (the medial condyle 6 in FIG. 2) is equal to the minimum thickness $t_3$ of bone resected at the posterior surface.

Figure 7:
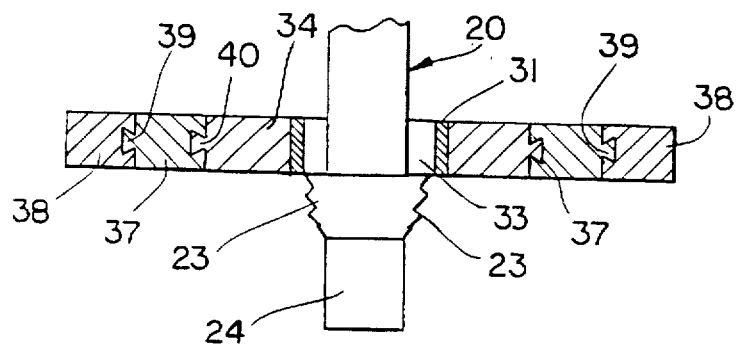
FIG. 7 is a sectional view taken on line 7—7 in FIG. 6.

In order to establish the precise positions of the three planar cuts 10, 11, 12 to be made on the femur 4, a referencing or datum system is utilized which in the description herein is in the form of an intramedullary rod 20 installed in a bore 21 formed in the femur. The use of the intramedullary rod 20 as a benchmark or datum is known in the art and is illustrated herein by way of example. Other referencing or datum systems can be employed as well, for example, utilizing two pins placed in the condyles a set distance below the anterior femoral cut to position an AP cutting guide thereon. This will be described later. The bore 21 is formed longitudinally in the shaft 9 and in the condylar region 4 of the femur at a location which is slightly anterior of the intercondylar notch 8. The rod 20 has a cylindrical portion 22 which snugly fits in the bore 21 but is able to be rotated in the bore 21. The rod 20 may include radial flutes 23 extending outwardly a distance slightly greater than the diameter of the bore 21. The flutes 23 are initially outside the bore 21 and are intended to be driven into the bore 21 to fixedly secure the rod 20 in the bore 21. For this purpose, the flutes 23 are tapered to facilitate driving them into the bore 21 and grip the bore tightly in the distal femur when driven therein. The outer ends of the flutes 23 can be saw-tooth or jagged as shown in FIG. 7 to provide a resilient gripping action. The rod 20 includes an adjunct end or stub 24 which is non-circular in cross-section. The stub 24 may extend at an angle with respect to the longitudinal axis of the rest of the shaft so as to be substantially perpendicular to the joint and the prospective distal end cut 12 and parallel to the weight bearing axis of the leg. Shafts having stubs with different angles may be provided and selection is made on the anatomical condition of the patient. This is conventional in prior usage.

The angular position of the non-circular stub 24 in bore 21 when the flutes 23 are driven into the bore 21 is a measure of the angle A at which the posterior and anterior cuts 11, 10 are made and, consequently, of the angular position of the knee prosthesis 5 on the femur relative to the weight bearing axis of the leg.

The anatomical conditions governing the angular position of the rod 20 in the bore 21 is based on anatomy to maintain a straight line between the hip joint, the center of the knee joint and the center of the ankle joint. If the rod 20 initially assumes an angular position parallel to plane T, the rod is rotated by angle A to reach its datum position from which the cuts 10, 11, 12 will eventually be made. Nominally, the rotation is at an angle of 3° to match the angle of the tibia prosthesis. However, due to wear of the condyles, and anatomical conditions of the patient the rotation of the rod must be varied from 3° to match the tibia prosthesis. The surgeon is readily able to estimate this angle based on the anatomy and on X-rays of the patient. Heretofore, however, the surgeon had to estimate the angle at which to set the rod 20 when the rod is driven into the bore 21. An imprecise estimate of the rotational orientation of the stub 24 can lead to angulation and placement errors of the prosthesis. Stated succinctly, the estimate by the surgeon of the angulation of cut 11 based on patient anatomy is accurate, but the "eyeballing" of the rotational position of the stub is often inaccurate.

The invention provides a tool or instrument 30 which is fitted on the stub 24 of rod 20 and accurately establishes rotation of the rod 20 when it is driven into the bore 21 and which measures the distance D' which in turn will determine the location of the planar cuts 10, 11, 12.

The tool 30 includes a sleeve 31 having a non-circular bore 32 of the same shape as the stub 24 in order to be fitted on the stub 24 for common rotation therewith. The sleeve 31 has grooves 33 aligned with flutes 23 to permit passage of the flutes 23 through the sleeve 31 when the rod 20 is driven into the bore 21 in the shaft 9 of the femur. The sleeve 31 is rotatably supported in a slider 34 which is slidably supported by a lower half 35 of a caliper means whose upper half 36 is slidably engaged with lower half 35. The upper and lower halves 36, 35 are formed as open U-shaped members forming adjacent legs 37, 38 which are slidably engaged by tongue and groove engagement means 39. The slider 34 is slidably engaged in the legs 37 of the lower half 35 of the caliper means by a tongue-and groove engagement means 40.

Figure 8:
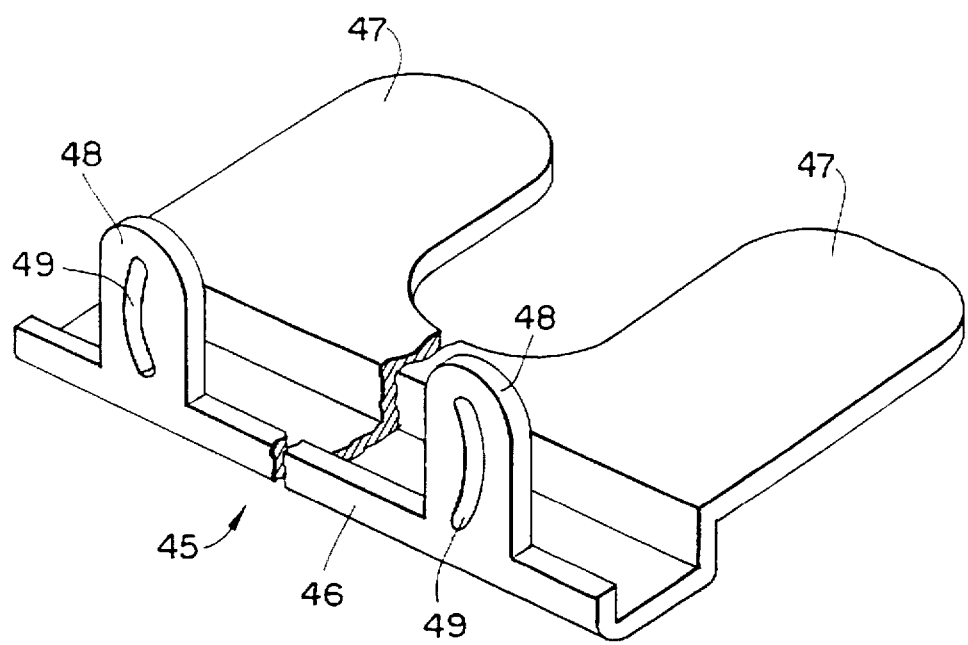
FIG. 8 is a broken, perspective view of a lower caliper feeler of the tool.

A cross leg 41 at the closed end of the lower half 35 of the caliper means engages a bar 42 for slidable movement in a direction substantially perpendicular to the direction of slidable movement of slider 34. The bar 42 is formed with opposed flats 43 on which the cross leg 41 can slide without undergoing rotation. The bar 42 is provided with forwardly facing pins 44 at end regions thereof. A posterior caliper 45 is mounted on the pins 44. The posterior caliper 45 includes a caliper plate 46 with spaced caliper feelers 47 (FIG. 8) for respectively contacting the posterior surfaces of the medial and lateral condyles. A pair of upright legs 48 are provided on plate 46 and the legs 48 are provided with respective slots 49 to receive respective pins 44 of bar 42. The slots 49 are part-circular in extent and have a common center such that either pin 44 can ride in its respective slot 49 and change the angle of bar 42 relative to the caliper plate 46. The ends of the pins 44 are threaded and nuts 50 are engaged on the threaded ends to lock the position of the pins 44 in the slots 49.

At the top of upper half 36 of the caliper means is an integral upstanding projection 60 which is integral with a guide bar 61. The guide bar 61 extends substantially perpendicular to the plane of the caliper halves 36, 37. The guide bar 61 has a bore 62 at one end thereof in which is slidably fitted an end of a rod 63 of an anterior caliper feeler 64 for extension and retraction adjustment movement of the anterior caliper feeler 64. A nut 65 secures the position of the rod 63. At the end of the rod 63 of the anterior caliper feeler 64 is a sector plate 66 which is pivotably supported at 67 by the rod 63. The sector plate 66 has a part-circular surface 68 adapted to contact the anterior surface 13 of the femoral cortex. The surface 68 has its center at the pivotable support point 67.

Figure 1:
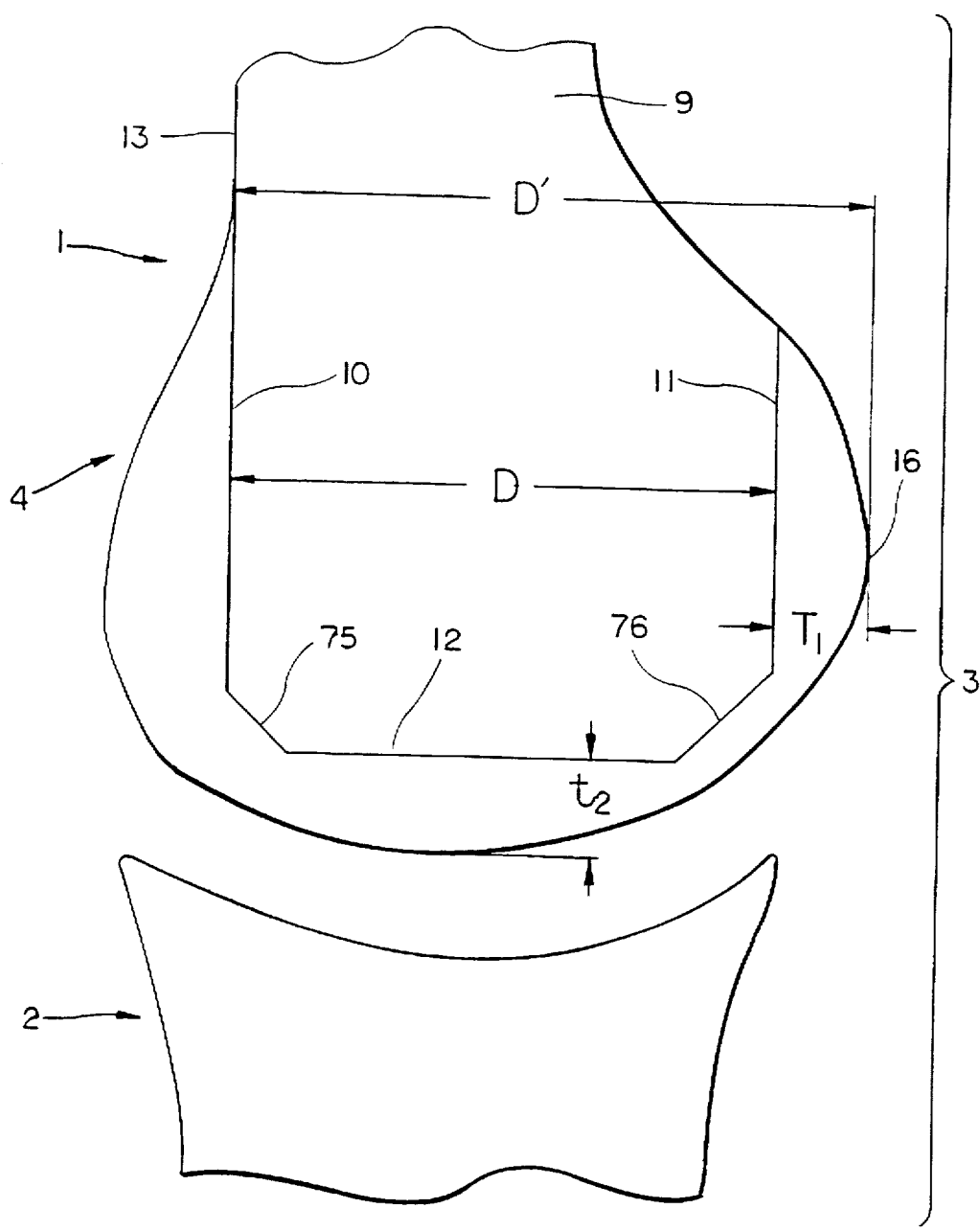
FIG. 1 is a diagrammatic, lateral view of the femur and tibia at a knee joint showing prospective cuts to be made on the femur for installation of a femoral prosthesis.
Figure 2:
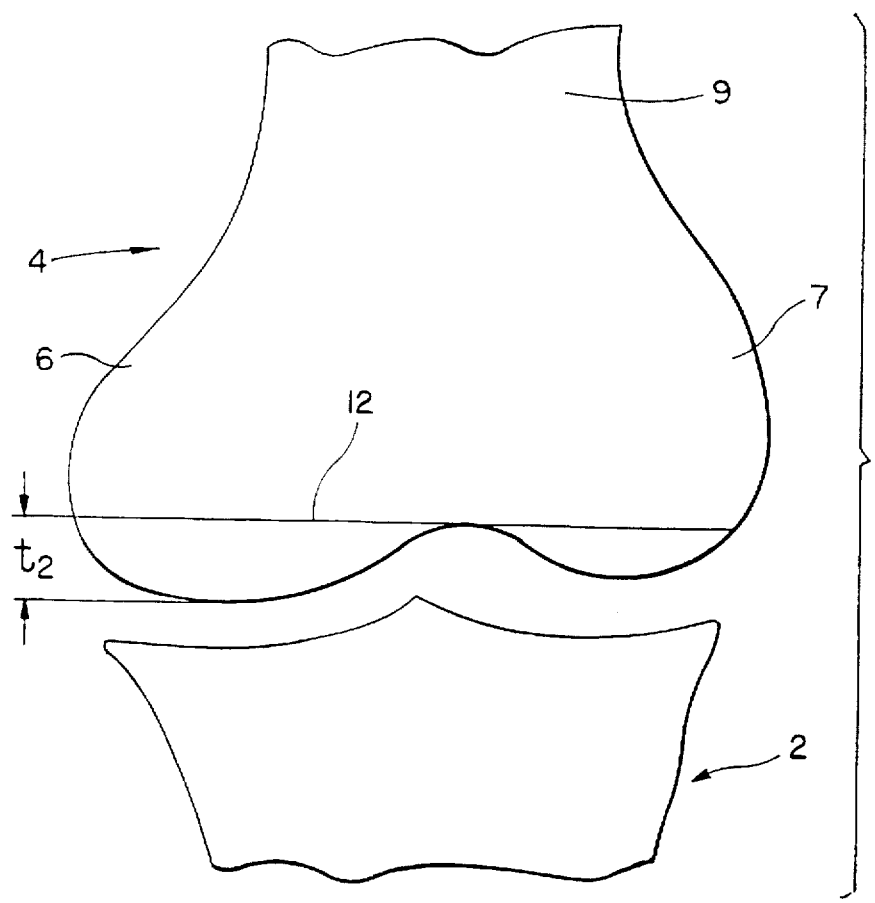
FIG. 2 is a diagrammatic illustration of the knee joint of FIG. 1 seen anteriorly of the joint.
Figure 5:
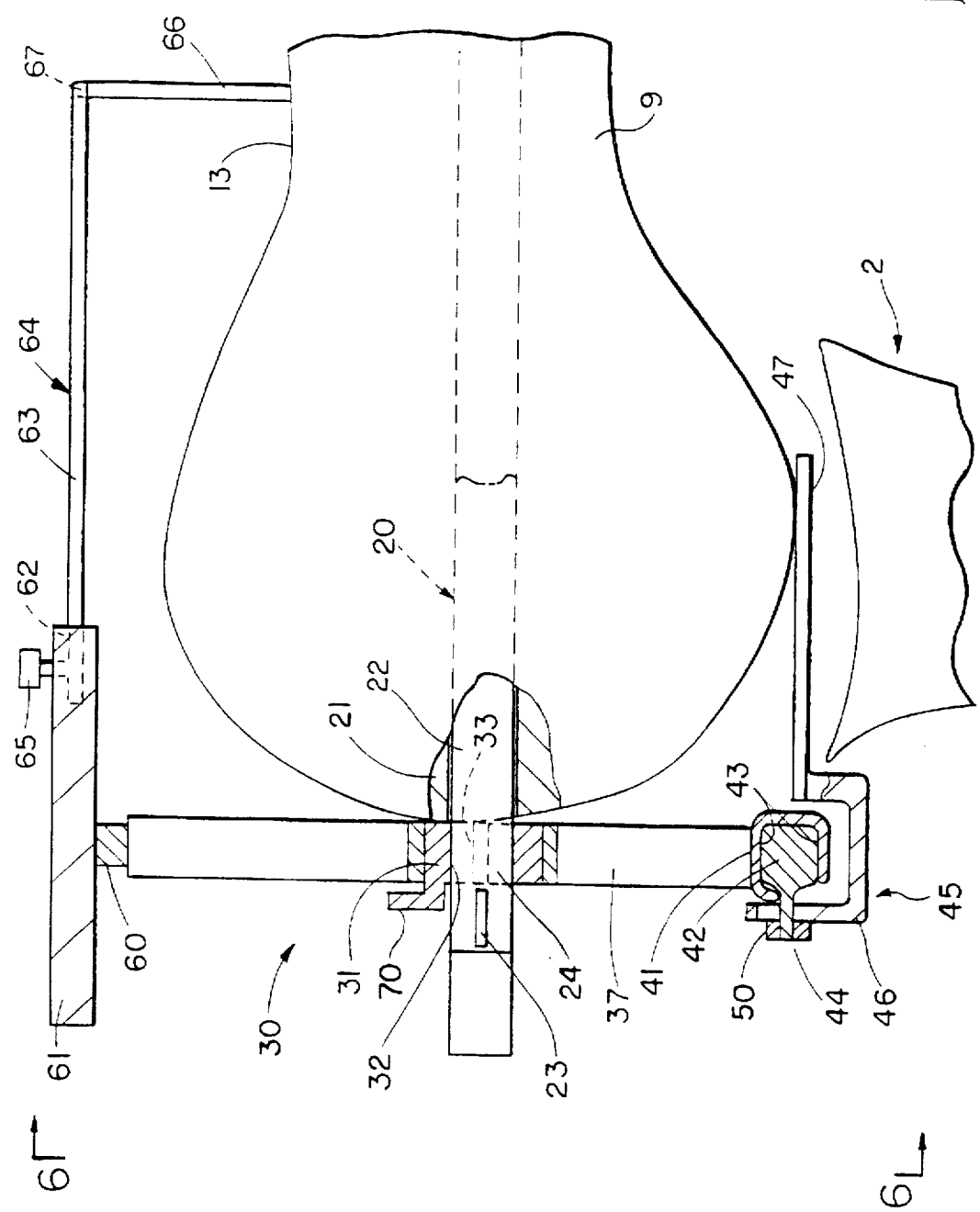
FIG. 5 is a side view similar to FIG. 1 in which the tibia has been turned 90° to expose the distal end of the femur, an intramedullary rod has been inserted into the femur and a tool placed on the rod, the tool being partly broken away and shown in section.
Figure 6:
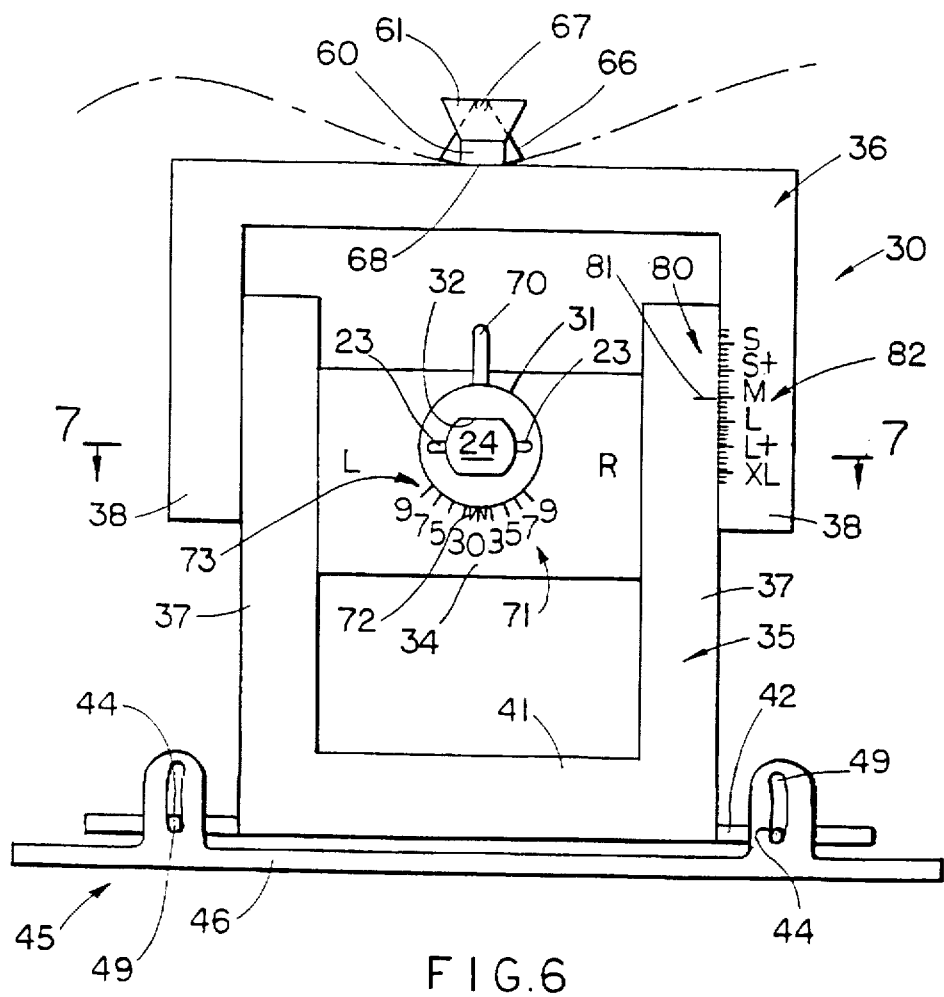
FIG. 6 is an end view of the tool taken in the direction of arrow 6—6 in FIG. 5.
Figure 9:
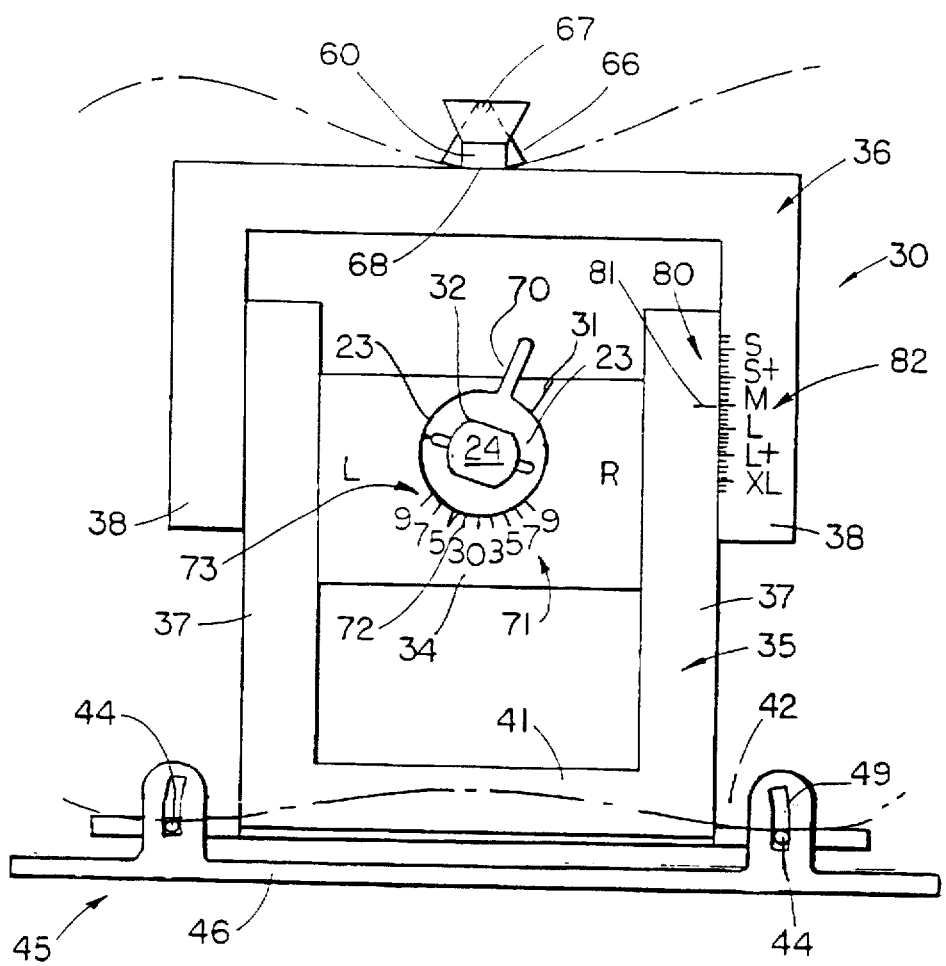
FIG. 9 is similar to FIG. 6 and illustrates a first stage in which the rod is angularly rotated by a specific amount.

In operation, the femur is rotated 90° from the position shown in FIG. 2 to the position in FIGS. 3 or 5 so that the distal end of the femur is exposed. The bore 21 is formed in the femur and the rod 20 is inserted into the bore 21. The tool 30 is then installed in the rod 20 by fitting the bore 32 in sleeve 31 on the stub 24 of the rod 20 projecting from the distal end of the femur. The posterior caliper feelers 47 are respectively brought into contact with the posterior surfaces of the respective medial and lateral condyles. This effectively establishes the position of plane T as described in FIG. 3. A radially projecting tab 70 on the sleeve 31 is manually engaged to rotate the sleeve 31 through angle A representing the angle determined by the surgeon as explained previously. A scale 71 is provided to indicate the angle through which the sleeve 31, and thereby the rod 20, has been turned. The scale comprises an index marker 72 on the sleeve and an angle scale 73 on the slider 34. The scale 73 is marked for left and right femurs and for left femurs (described and illustrated in the drawing) the sleeve and rod are rotated to the right (clockwise) whereas when the tool is mounted on a rod in the right femur, the sleeve and rod are rotated to the left (counter clockwise). When the scale 71 indicates the desired angle of rotation, the sleeve 31 is rotatably locked in the slider 34 by suitable means (not shown) and the rod 20 is driven into the bore 21 of the femur to be angularly secured thereon in the desired rotational position relative to the plane T tangential to the posterior surfaces of the medial and lateral condyles. This is the position shown in FIG. 9.

Figure 10:
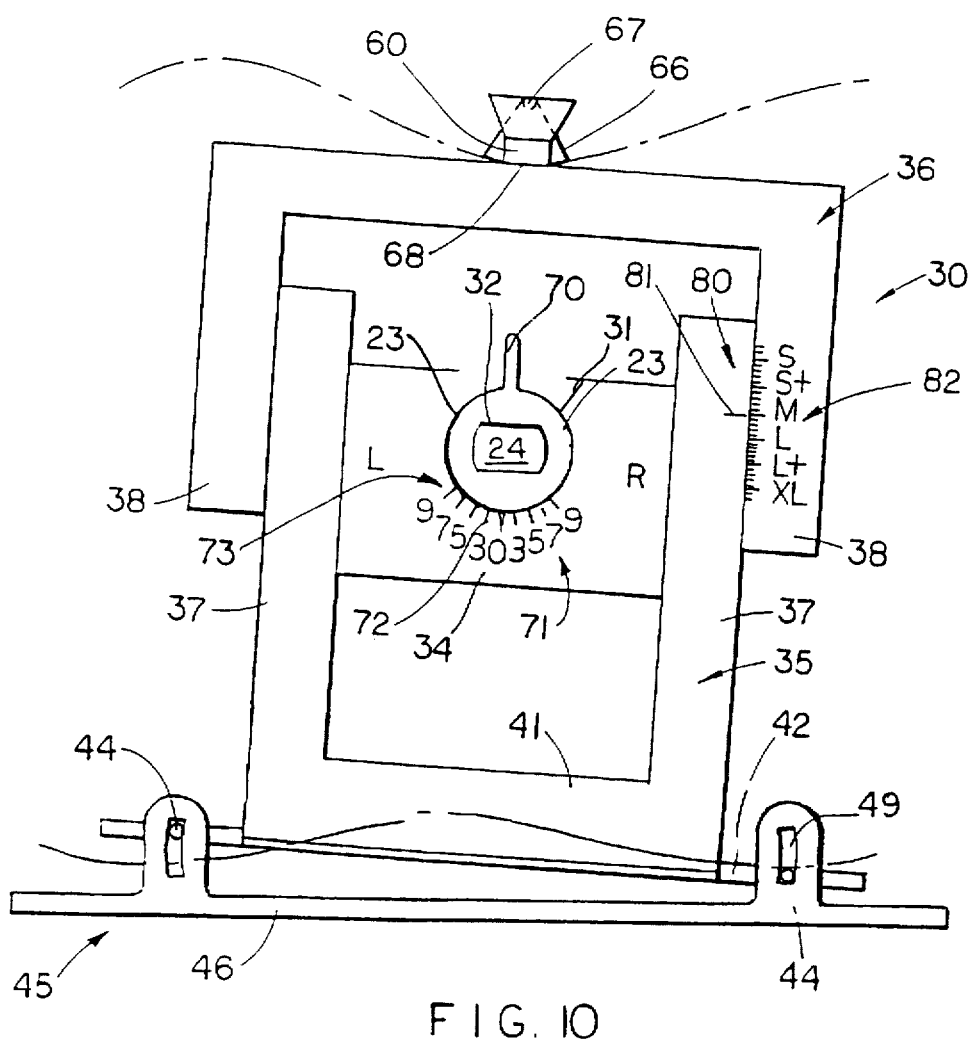
FIG. 10 is similar to FIG. 9 in a subsequent stage.
Figure 11:
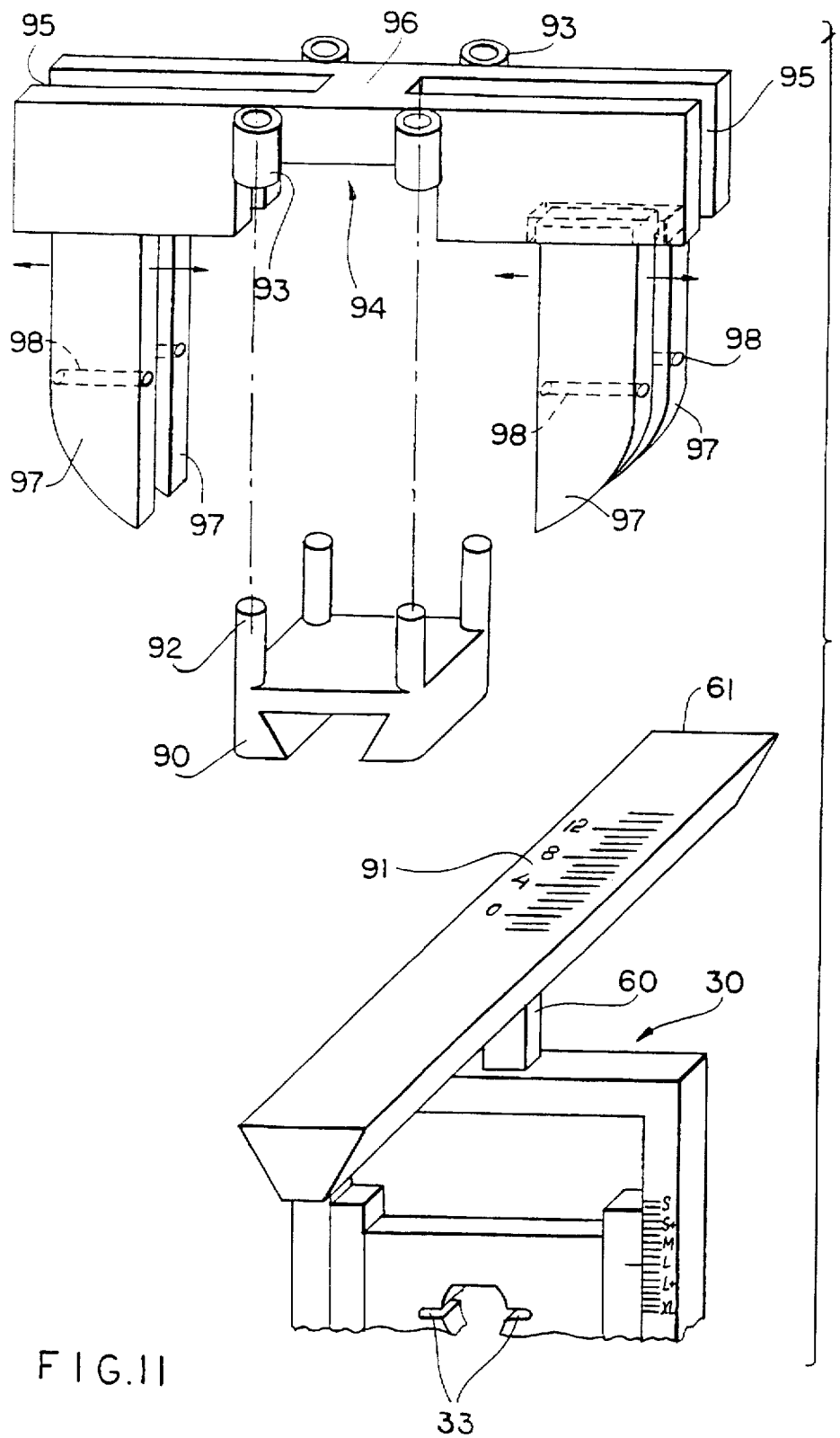
FIG. 11 is an exploded view showing a cutting guide to be installed on the tool.
Figure 12:
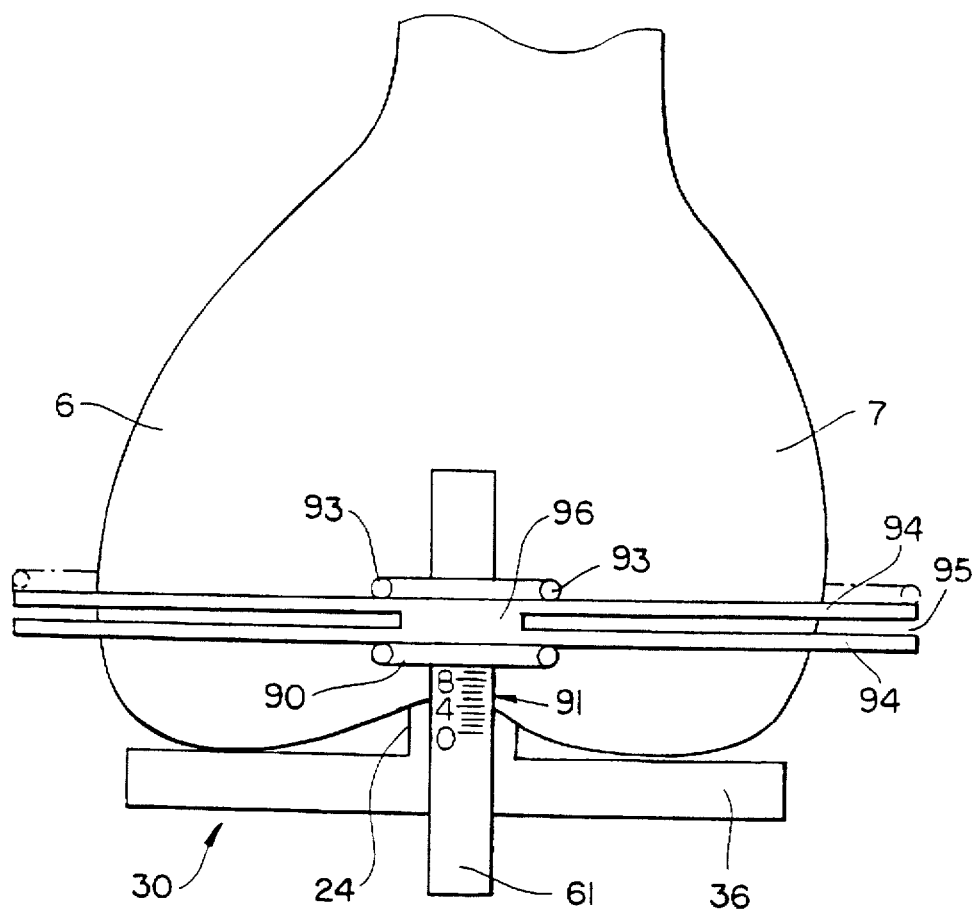
FIG. 12 is a top, plan view showing the cutting guide installed on the tool.

In order to set the caliper means in position to measure the distance D', the nuts 50 on pins 44 are loosened and the upper and lower caliper halves 36 and 37 are rotated as a unit around pin 44 at the lateral femoral condyle until the index marker 72 returns to its zero setting on the scale 73 as shown in FIG. 10. The nuts 50 are then tightened and the caliper halves are now in a position to measure distances perpendicular to the plane P tangent to the posterior surface of the lateral condyle. The capability of slidable movement of the slider 34 on the lower caliper half 35 and of the caliper half 35 relative to bar 42 and posterior caliper feeler 45 permits the rotation of the caliper halves about pin 44 at the lateral condyle while the sleeve 31 and the slider 34 are engaged with the stub 24 of rod 20.

The anterior feeler 64 is then positioned so that sector plate 66 contacts the anterior surface 13 of the femoral cortex. A distance scale 80 is provided between the upper and lower caliper halves 36, 35 and comprises a marker 81 on leg 37 and a scale 82 on leg 38. The scale 82 indicates the prosthesis size and hence is a measure of the distance D. The calibration is such that when the marker 81 is in correspondence with a mark on scale 82 for a particular prosthesis, when this prosthesis is utilized, the difference between D and D' (the thickness $t_3$ resected at the posterior condyle) will be substantially equal to the thickness of the prosthesis to be inserted. If the scale falls between prosthesis markings on scale 82, generally the smaller prosthesis is selected and the resected thickness of the lateral condyle will be slightly increased accordingly. The scale markings can also be calibrated with reference to the resected thickness $t_1$ at the medial condyle to reflect the normally greater thickness resected thereat.

With the tool still mounted on the rod 20, the anterior feeler 64 is removed and a guide 90 is slidably fitted on guide bar 61. At the top of the guide bar 61 another scale 91 is provided. The scale 91 is marked in millimeters and represents the distance from a plane perpendicular to the rod and tangent to the high point of the distal end surface of the more prominent of the medial or lateral condyles. In other words, when the tool 30 remains on the rod 20 and is brought into abutment with the condyles, this is the zero position of the scale 91. The guide 90 has four upstanding pegs 92 which fit into four holes 93 of a distal end cutting guide 94.

The cutting guide 94 is provided with slots 95 extending in a plane substantially perpendicular to the axis of stub 24. The slots 95 extend from the medial and lateral side surfaces of the cutting guide 94 towards the center thereof. The slots 95 are adapted to guide a narrow cutting blade (not shown) for respectively cutting the medial and lateral condyles 6, 7 along planar cut 12. The slots 95 are separated by a solid, intermediate section 96. The position of the slots 95 relative to the scale indicate the thickness $t_2$ to be resected by the planar cut 12 at the distal end of the femur. The invention contemplates that the thickness $t_2$ may be equal to the thickness $t_3$ determined by the measurement of distance D'. Therefore, the guide 90 is moved until the slots 95 are aligned with the distance on scale 91 equal to the determined thickness $t_3$. The guide 90 is then locked on guide bar 61 by suitable means (not shown). Depending feet 97 are slidably mounted on cutting guide 94 in respective pairs on opposite sides of each slot 95. After the cutting guide 94 has been moved to its cutting position as indicated on scale 91, the depending feet 97 are slidably moved to abut against respective portions of the condyles. The feet 97 are provided with nail holes 98 and nails (not shown) are driven into the holes 98 to secure the cutting guide 94 to the femur. A conventional cutting blade is then inserted in guide slots 95 to cut the distal ends of the condyles 6, 7 along the planar cut 12. The feet 97 nailed to the condyles prevent skewing or sliding of the cutting guide during the cutting operation.

Figure 13:
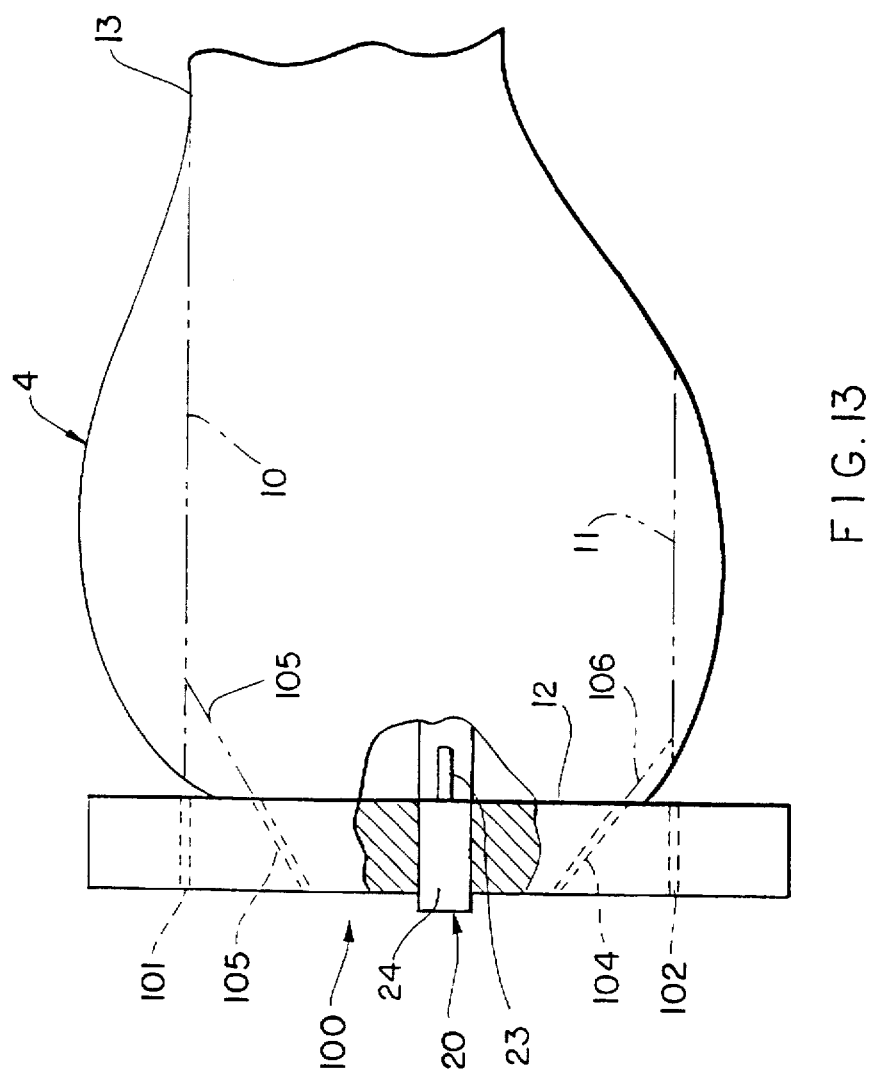
FIG. 13 illustrates the distal end of the femur after the distal end has been cut and an AP cutting guide has been placed on the rod.

The tool 30 is then removed from the rod 20 and a conventional AP cutting guide 100 (FIG. 13) is fitted on the end of the rod 20 and abutted against the planar surface 12 now cut at the distal end of the femur. The cutting guide 100 is provided with guide slots 101 and 102 which can be precisely placed for guiding a cutting blade to produce the anterior and posterior cuts 10, 11 respectively. The cut 10 will be flush with the anterior surface 13 of the femoral cortex and the cut 11 will be at distance D therefrom. The AP cutting guide 100 also includes angular slots 103, 104 to form chamfer cuts 105, 106 on the femur which match corresponding angular surfaces 107, 108 on the knee prosthesis 5.

Figure 14:
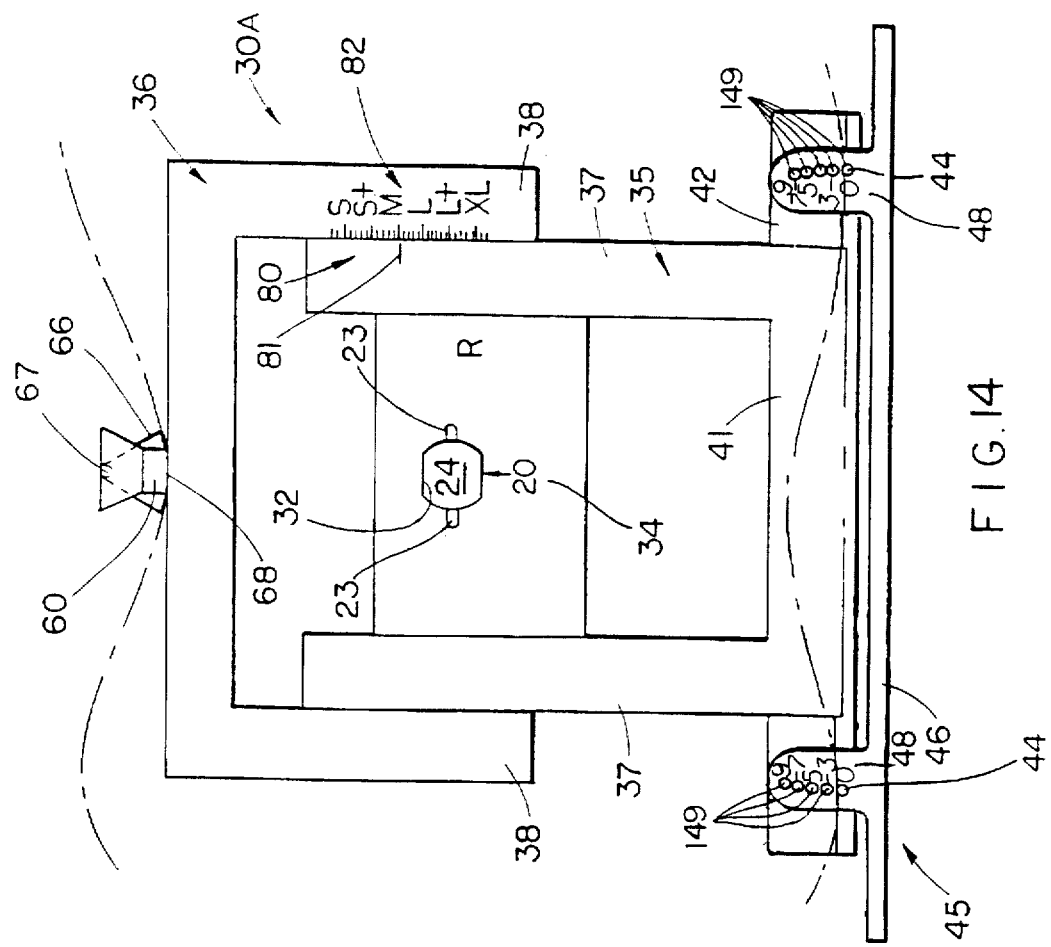
FIG. 14 is an end view similar to FIG. 6 of a second embodiment of the tool.
Figure 15:
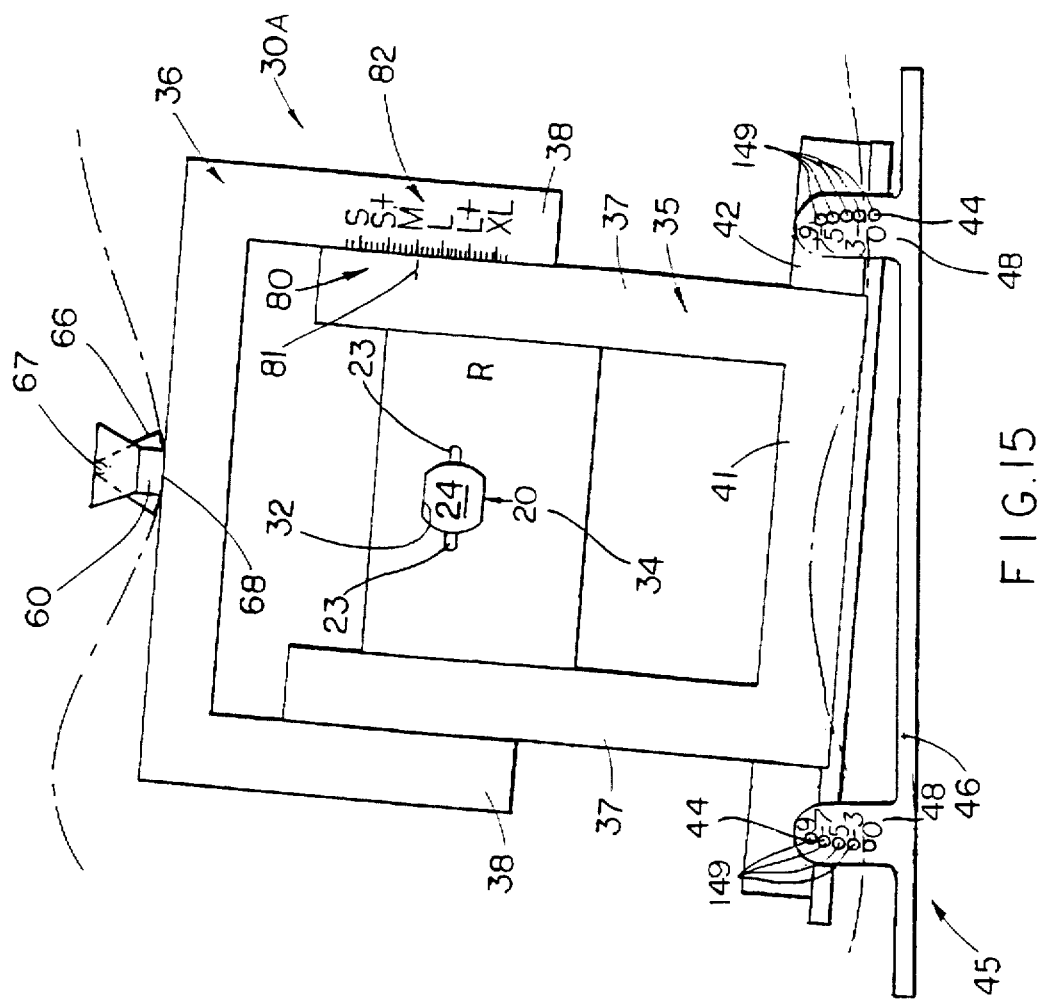
FIG. 15 shows the tool of FIG. 14 in a rotated state.

FIGS. 14 and 15 illustrates a second embodiment of a tool 30A which is a simpler version of the first embodiment of FIGS. 5–10 and wherein the same reference characters are used to designate like elements.

Essentially, the embodiment of the tool 30A of FIGS. 14 and 15 differs from that of FIGS. 5–10 in eliminating the rotatable sleeve 31 and directly engaging the stub 24 of rod 20 in bore 32 now provided directly in the slider 34. The slider 34 thus serves as the engaging means for the stub 24. The legs 48 on the caliper plate 46 are provided with spaced holes 149 instead of the continuous slot 49 of the embodiment of FIGS. 5–10 and angular markings 173 are provided adjacent to the holes 149 to indicate the magnitude of angle A between the caliper plate 46 and bar 42, serving as a measurement plate, when the pin 44 is in the respective hole 149. In the illustrated embodiment in FIGS. 14 and 15, the holes 149 are placed to provide angulations of 0°, 3°, 5°, 7° and 9° left and right between bar 42 and caliper plate 46.

In operation, the stub 24 is engaged in the bore 32 in slider 34 and pins 44 are placed in the 0° holes in respective legs 48. The caliper feelers 47 are placed into tangential contact with the posterior surfaces of the medial and lateral condyles 6, 7 respectively. The pin 44 in the leg 48 corresponding to the medial condyle is then removed from the 0° hole and placed in the hole 149 corresponding to the desired angulation of the rod 20. This is shown in FIG. 15 where pin 44 is set in the hole 149 to angulate the bar 42, 7° relative to the caliper plate 46 and thereby relative to the plane T tangent to the medial and lateral condyles. By virtue of the slidable support of slider 34 in legs 37 and the slidable support of cross leg 41 on bar 42, the tool 30A is capable of remaining in position on stub 24 and rotating around pin 44 at the posterior surface of the lateral condyle 7.

The measurement by the caliper means to determine the size of the prosthesis and the resected thickness $t_3$ at the lateral condyle is carried out in the same way as in the first embodiment and the planar cuts are then made on the condyles as previously described.

As was described for the first embodiment of tool 30, it is also possible to effect measurement with the tool 30A to determine thickness $t_1$ at the medial condyle and to utilize this thickness to establish the thickness $t_2$ for the distal cut 12.

Both the first and second embodiments have been described with regard to the intramedullary rod 20 with radial flutes 23 to embed the rod securely in the bore 21 in the femur to establish the datum or benchmark position for attaching the cutting guide 60 to effect the distal end cut 12 and thereafter the AP cutting guide 100 to effect the anterior and posterior planar cuts 10, 11. However, other suitable means can be employed to secure the angular position of the rod instead of the flutes 23. Moreover, since the rod 20 is ultimately removed from the femur after the planar cuts 10, 11, 12 have been made, the absence of the flutes 23 makes removal simpler.

Figure 16:
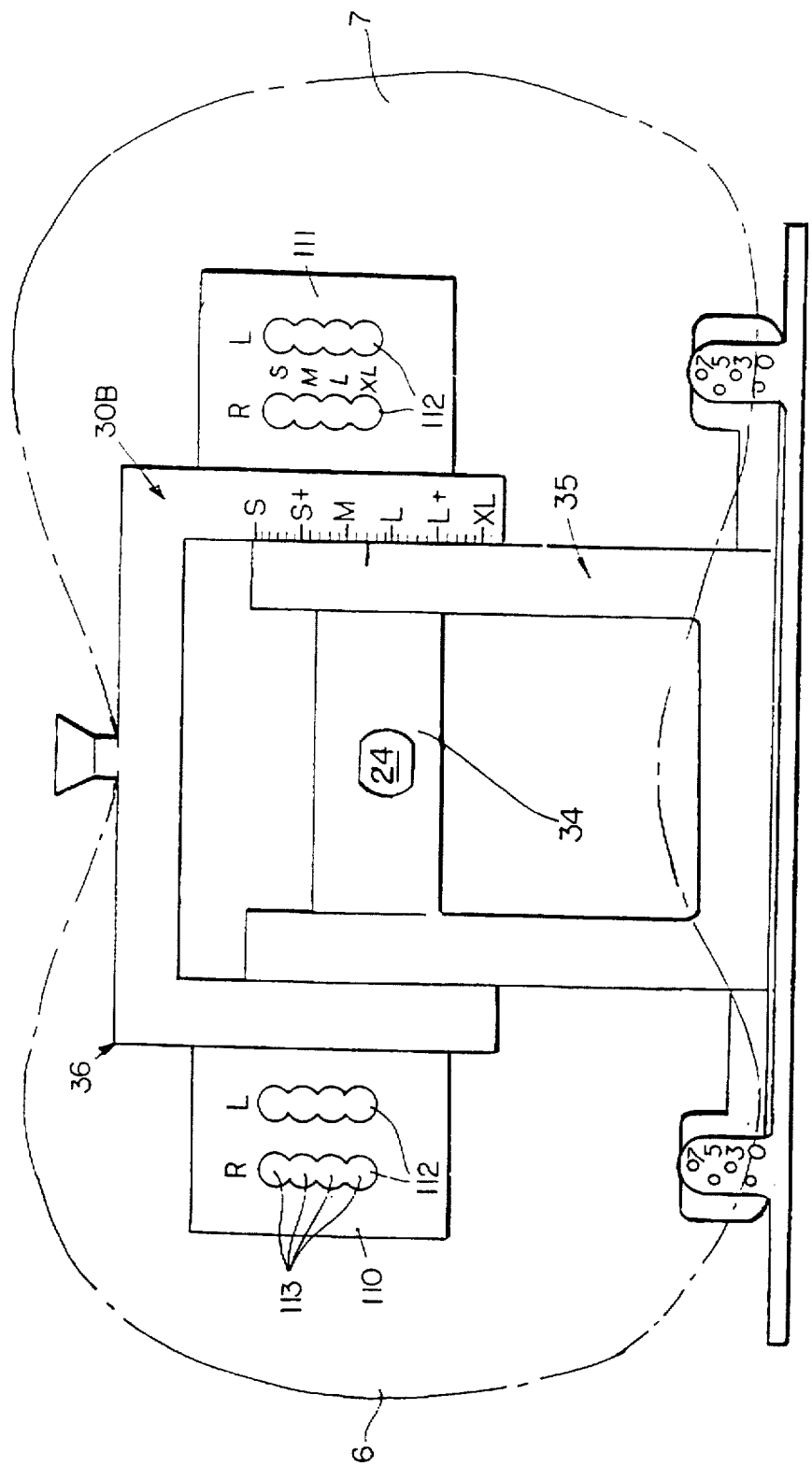
FIG. 16 is an end view similar to FIG. 6 of a third embodiment of the tool.
Figure 17:
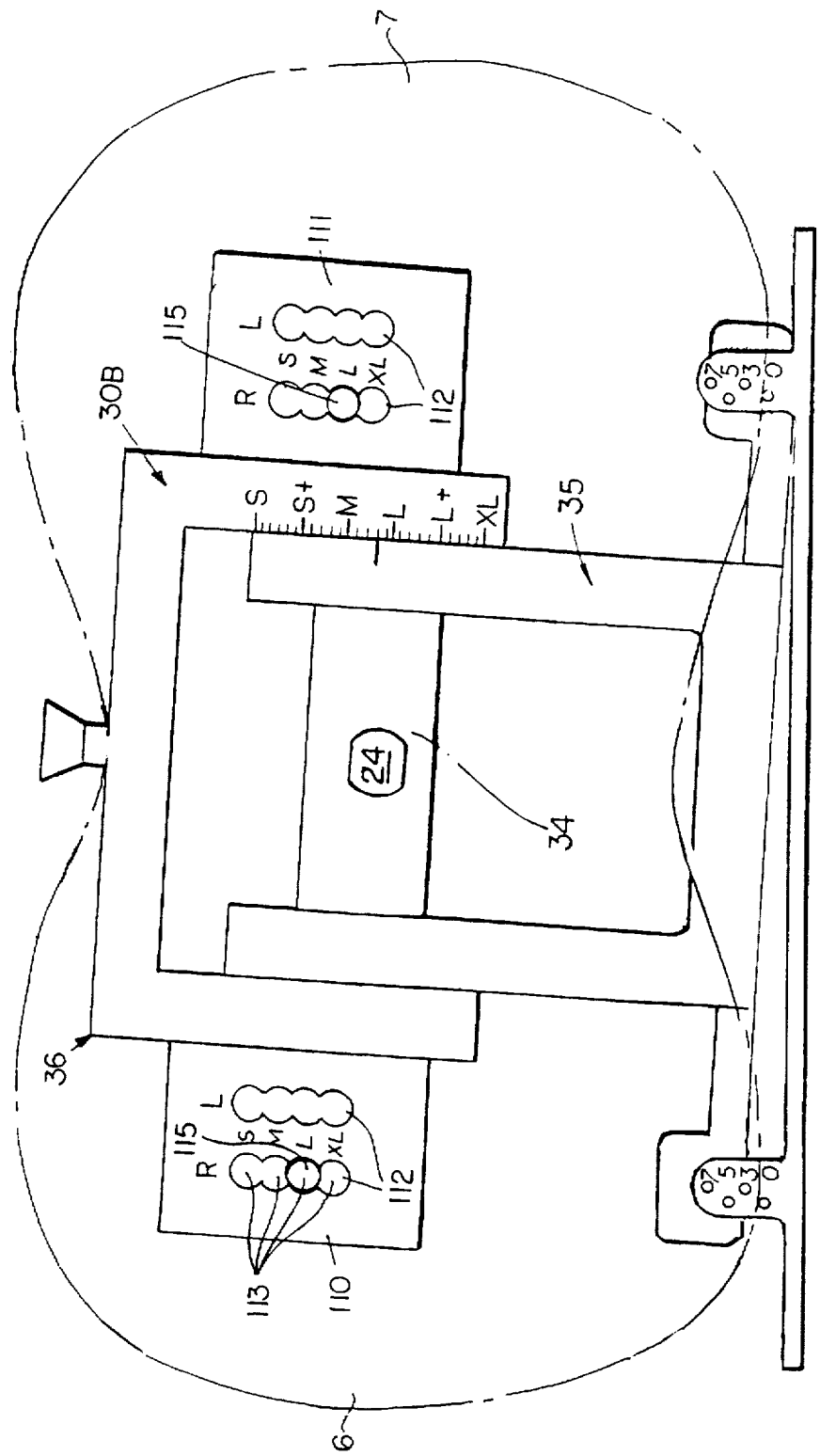
FIG. 17 shows the tool of FIG. 16 in a rotated state.

FIGS. 16 and 17 illustrate a third modified embodiment of the tool 30B which secures the angular datum position by use of a rod without flutes 23. The same reference characters as in the first two embodiments designate like elements.

In the third embodiment, the rod 20 is smooth and devoid of flutes 23. The rod 20 is rotated to its adjusted angular position, as in the first and second embodiments, and in order to secure an angularly adjusted datum position, lateral plates 110, 111 are secured to the legs 38 of the upper caliper half 36. Each plate 110, 111 contains two vertical rows 112 of overlapped holes 113. The rows 112 are designated for right and left femurs and the holes 113 are respectively graduated in size order from the scale 82. When the caliper means of the tool 30B has been rotated to the desired degree of angulation, pins 115 or similar fasteners are placed in the appropriate holes 113 in the lateral plates 110, 111 and secured in the distal ends of the medial and lateral condyles so that the pins 115 project from the distal ends of the condyles. The pins 115 establish an angular datum position representing the rotation of the tool. The steps of measurement of prosthesis size, and of effecting the planar cut with the guide 60 are carried out as in the previously described embodiments. However, after the distal end cut 12 is made, the tool 30B is removed leaving the pins 115 in place in the condyles, the rod 20 is removed from the femur, and a guide 100' is mounted on the pins 115 which serve to accurately position the guide 100' so that the slots 101–104 will be precisely located for exact placement of the cuts 10, 11, 105 and 106. The guide 100' has holes 116 to receive the pins 115 which are precisely located with regard to the slots 101–104 to insure accurate location of the cuts when the guide 100' is mounted on the pins 115. After the cuts have been made, the pins 115 are removed from the condyles. As evident from the above, this embodiment contemplates the use of the pins 115 as the means to provide the datum position for the cutting guide 100' in lieu of the rod 20. The use of the plates 110, 111 and of the pins 115 is applicable to the other embodiments as well.

Figure 18:
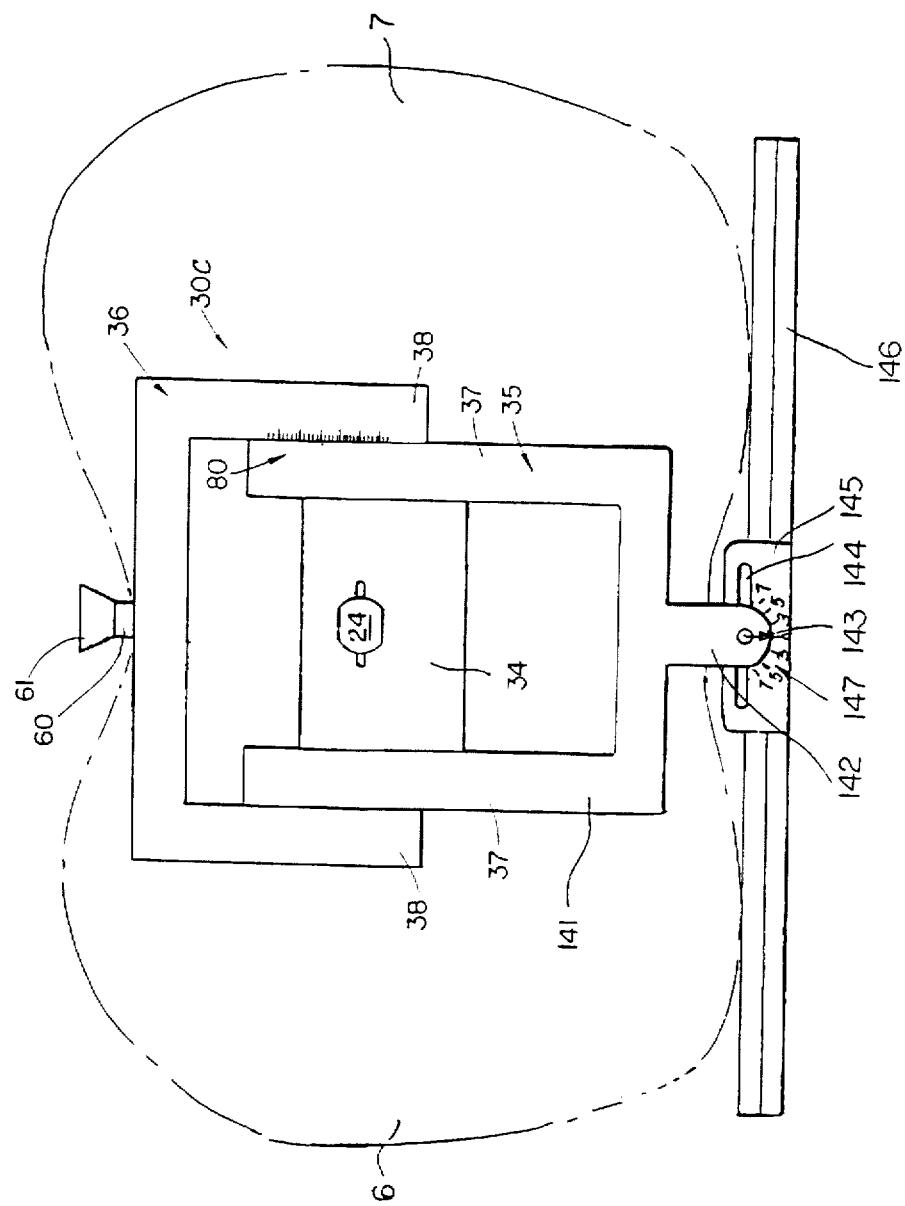
FIG. 18 is a view similar to FIG. 6 of a fourth embodiment of the tool.
Figure 19:
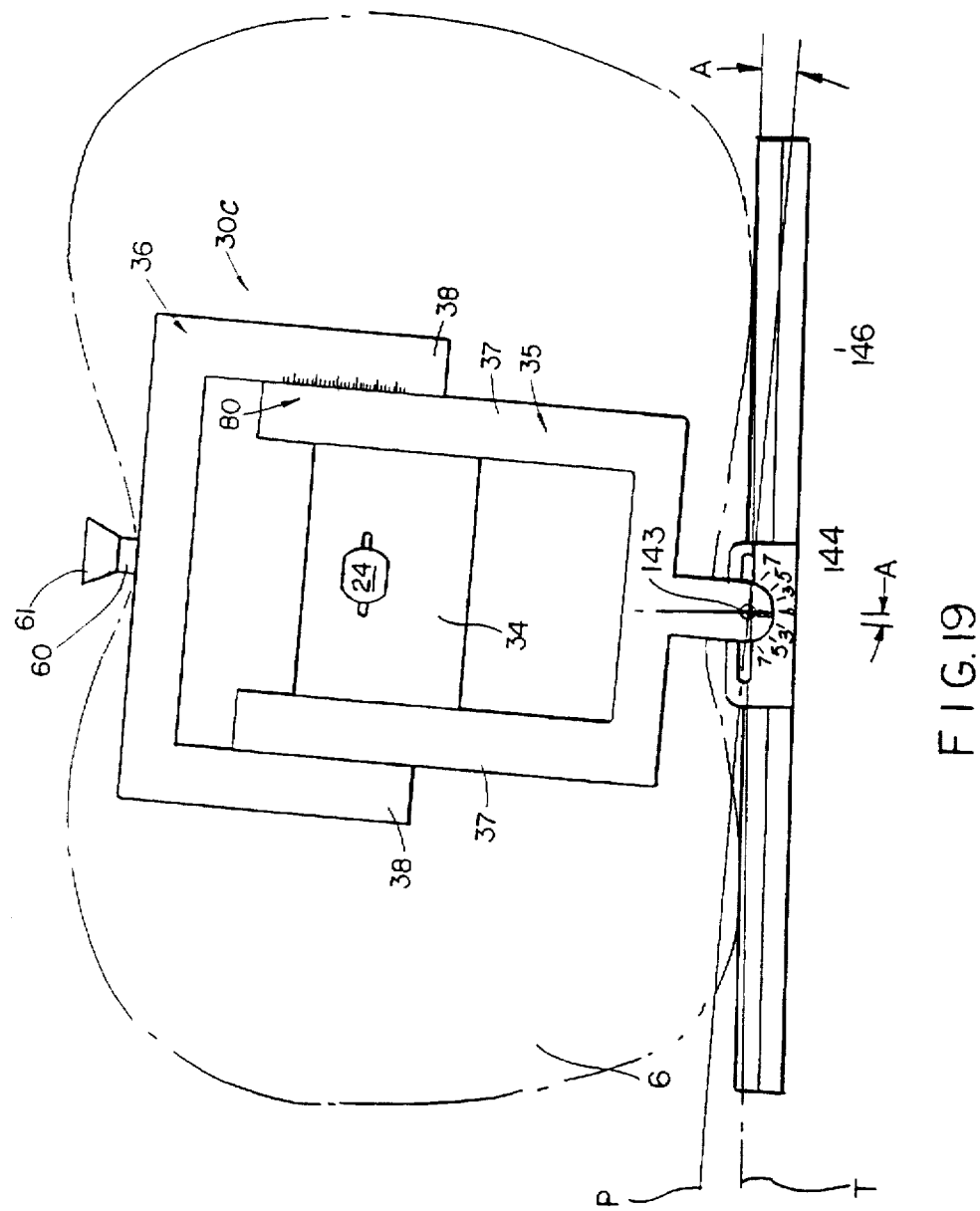
FIG. 19 shows the tool of FIG. 18 in a rotated state.
Figure 20:
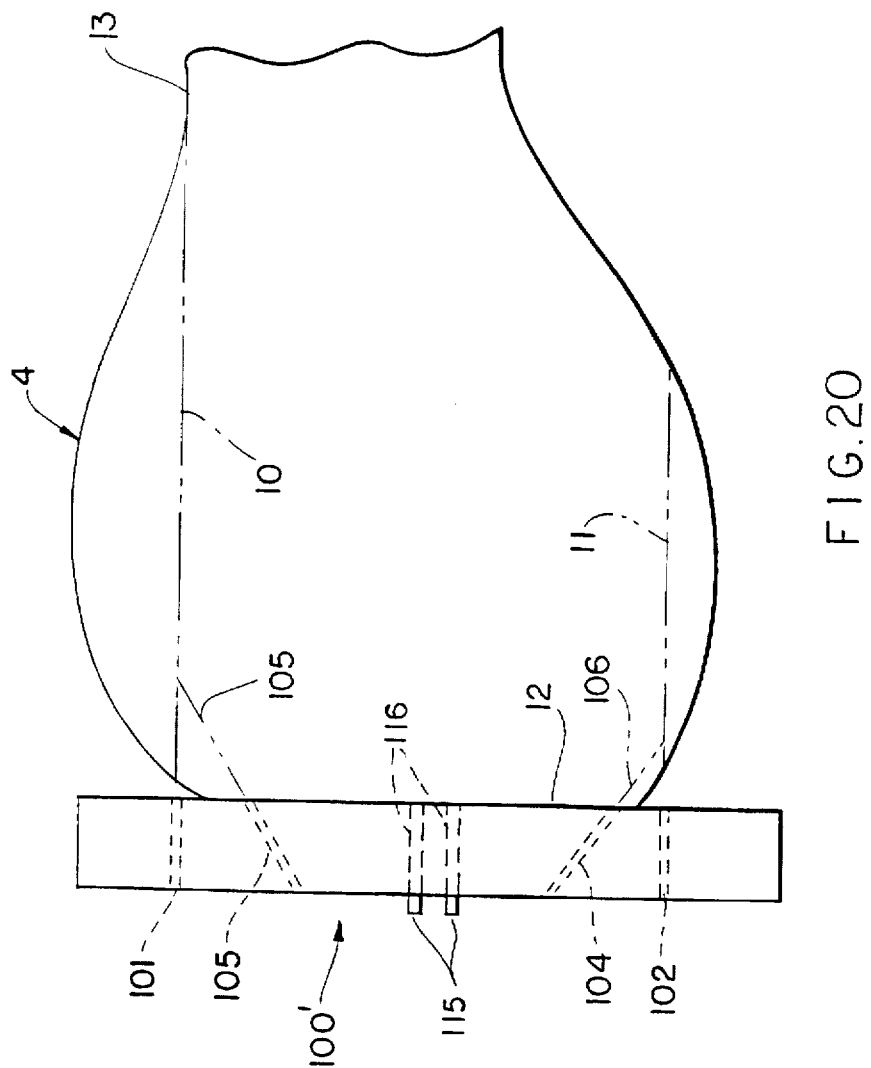
FIG. 20 is similar to FIG. 13 but shows a modification adapted to the embodiment of FIGS. 16 and 17.

FIGS. 18 and 19 illustrate a fourth modified embodiment of the tool 30C which is a simplified version of the second embodiment of FIG. 14 and uses the same reference characters to designate like elements.

The tool 30C utilizes slider 34 which engages the rod end 24 and is slidably engaged in the legs 37 of the lower caliper half 35. The legs 37 of the lower caliper half 35 are slidably engaged with the legs 38 of the upper caliper half 36.

At its lower end, the lower caliper half 35 includes a cross bar 141 from which a leg 142 depends. The leg 142 supports a pivot 143 which slidably rides in a slot 144 in a bracket 145 integral with posterior caliper plate 146. The posterior caliper plate 146 is similar to caliper plate 46 of the second embodiment and includes posterior caliper feelers for contacting the medial and lateral condyles 6 and 7. The slot 144 extends substantially parallel to the caliper plate 146 in the plane of tangential contact of the posterior feelers with the posterior surfaces of the medial and lateral condyles. An angle scale 147 is provided between the leg 142 and the bracket 145.

In the initial position of the tool, the slider 34 is fitted on the end 24 of the rod and the posterior feelers are brought into tangential contact with the medial and lateral condyles. The caliper means 35, 36 are rotated, while the rod 24 is held fixed, until the angle scale 147 reads zero. The pivot 143 is disposed in the slot 144 substantially in the plane T tangent to the posterior surfaces of the medial and lateral condyles. The tool 30C is then rotated to cause the end 24 to rotate through an angle A corresponding to the determined angle of rotation. The angle A is read on the angle scale 147. The pin 143 undergoes slidable movement in slot 144 while the slider 34 undergoes slidable movement in lower caliper half 35 to accommodate the rotation of the tool. The pin 144 remains in the tangential plane T. The scale 80 is a measure of the distance from the anterior feeler in contact with the anterior femoral cortex and the pin 143 along a perpendicular line from the anterior femoral cortex to a plane P passing through the pin 144 and inclined relative to posterior caliper plate 146 by the angle of rotation A of the tool. Any difference between the distance from pivot point 67 to the surface 68 of the sector plate 66 and the corresponding distance measured along the perpendicular to the inclined plane P is negligible and even for an angle A of 12° the difference will be less than one-third mm.

As an alternative to the slot 144, the bracket 145 can be provided with a series of holes representing different angles of the caliper means 35, 36 relative to the plate 146, corresponding to different angles A, as in FIG. 14. The holes are provided along the axis of slot 144 in order to be in the tangential plane T of the posterior feelers on the posterior surfaces of the condyles. When the pin 143 is secured in a respective hole the caliper means is secured at the angle designated by the associated hole. In the use of this alternative, with the tool not yet fitted on the end 24, the angle of the caliper means is set by inserting the pin 143 into the selected hole and the posterior feelers on plate 146 are brought into tangential contact with the condyles 6, 7. The tool is then fitted on the end 24 which now assumes the angle of the caliper means relative to the plate 146. The rod 20 is then driven into the femur as before, or alternatively, as in the embodiment of FIGS. 16 and 17, pins 115 are installed in the condyles through holes in plates 110, 111 installed on the upper caliper half of the tool. The subsequent operations are the same as previously described.

Although the invention has been described with reference to specific embodiments thereof, it will become apparent to those skilled in the art that numerous modifications and variations can be made within the scope and spirit of the invention as defined in the attached claims.

What is claimed is:

1. A method for forming planar resections on the medial and lateral condyles of a femur of a knee to form seating surfaces to receive a femoral prosthesis and to properly articulate with a tibial and patellar prosthesis, said method comprising:

determining a prospective planar resection to be made at the posterior medial and lateral condyles of a femur at which a distance between an anterior surface of the femoral cortex and the prospective planar resection is substantially equal to an interior dimension of a femoral prosthesis to be fitted on said femur, said planar resection producing resection of the medial and lateral condyles at said posterior surface of respective thicknesses which are not necessarily equal, measuring the thicknesses which will be resected by said planar resection at said medial and lateral condyles at said posterior surface, resecting a distal end of the medial and lateral condyles along a plane which produces respective resected thicknesses, not necessarily equal, at said medial and lateral condyles and wherein the distal medial resection is substantially equal to the measured posterior medial condyle thickness to be resected and the distal lateral resection is substantially equal to the measured posterior lateral condyle thickness to be resected, and resecting the medial and lateral condyles along a plane at the anterior surfaces thereof substantially flush with the anterior surface of the femoral cortex, and along said prospective planar resection.

2. A method as claimed in claim 1, comprising loosely engaging a longitudinal rod in the femur such that an end of the rod projects from the femur, mounting a tool on the projecting end of the rod, and establishing, by said tool, an angular or rotational position of said prospective planar resection at a determined angle with respect to a tangential plane at the posterior surfaces of the medial and lateral condyles.

3. A method as claimed in claim 1, comprising indicating on said tool a value representative of said one thickness to be resected at said posterior surfaces of the medial and lateral condyles.

4. A method as claimed in claim 1, comprising providing a scale on said tool representing different sizes of prostheses, said scale accounting for differences in size between the distance between the anterior surface of the femoral cortex and a plane tangent to the posterior surface of one of the medial and lateral condyles, and a prosthetic size.

5. A method as claimed in claim 1, comprising positioning said prospective planar resection at an angle relative to a plane tangent to said medial and lateral condyles at said posterior surfaces thereof.

6. A method as claimed in claim 1, comprising loosely supporting a longitudinal intramedullary rod in the femur to serve as a datum, mounting a tool on said rod, angularly rotating said tool to a particular angle relative to a tangential plane tangent to the posterior surfaces of the medial and lateral condyles, fixedly securing said tool relative to the femur at said particular angle, providing a caliper on said tool and rotating said caliper with said tool around an axis located in said tangential plane through an angle equal to said particular angle when said tool is rotated, and mounting a cutting guide on said tool to effect said distal planar resection on said condyles.

7. A method as claimed in claim 6, comprising locating said axis in said tangential plane at the posterior surfaces of said condyles.

8. A method as claimed in claim 6, comprising securing said cutting guide to said condyles while resecting the distal ends of the medial and lateral condyles.

9. A method as claimed in claim 2, comprising securing two pins in said condyles in accordance with the angular or rotational position established by said tool to serve as a datum, said pins holding the tool in said angular or rotational position, mounting a cutting guide on the tool while the tool remains angularly secured on said pins, using said cutting guide to resect the distal planar resection on the condyles, removing the tool from the pins, mounting a second cutting guide on said pins and using said second cutting guide to obtain the resections at the posterior and anterior surfaces.

10. A method as claimed in claim 9, comprising providing a caliper on said tool and rotating said caliper with said tool around an axis located in said tangential plane through an angle equal to said determined angle when said rod is rotated.

11. A method as claimed in claim 9, comprising securing said cutting guide to said condyles while resecting the distal ends of the medial and lateral condyles.

12. A method for forming three planar resections on the medial and lateral condyles of a femur to form seating surfaces to receive a femoral prosthesis and to properly articulate with a tibial and patellar prosthesis, said method comprising:

determining a prospective planar resection to be made at the posterior of the medial and lateral condyles of a femur at which a distance between an anterior surface of the femoral cortex and the prospective planar resection is substantially equal to an interior dimension of a femoral prosthesis to be fitted on said femur, measuring a thickness to be resected by said prospective planar resection at the posterior surface of the medial and lateral condyles by measuring a distance between said anterior surface of the femoral cortex and a plane parallel to said prospective planar resection, resecting distal ends of the medial and lateral condyles along a plane which produces respective resected thicknesses, not necessarily equal, at said medial and lateral condyles and wherein the distal medial resection is substantially equal to the measured posterior medial condyle thickness to be resected and the distal lateral resection is substantially equal to the measured posterior lateral condyle thickness to be resected, and resecting the medial and lateral condyles along a plane at the anterior surfaces thereof substantially flush with the anterior surface of the femoral cortex, and along a plane containing said prospective planar resection.

13. A method as claimed in claim 12, comprising loosely supporting a longitudinal intramedullary rod in the femur as a datum, mounting a tool on said rod, angularly rotating said tool to a particular angle relative to a plane tangent to the posterior surfaces of the medial and lateral condyles. fixedly securing said tool relative to the femur at said particular angle, rotating a caliper of said tool around an axis located in said plane tangent to said posterior surfaces of said medial and lateral condyles through an angle equal to said particular angle by which said tool is rotated, and counting a cutting guide on said tool to effect said resecting of the distal ends of said condyles.

14. A method as claimed in claim 13, comprising indicating on said tool the size of a prosthesis based on said distance measured between said anterior surface of the femoral cortex and said plane tangent to the posterior surface of said one condyle, and indicating a difference between the measured distance and a prosthetic size.

15. A method as claimed in claim 13, comprising securing said cutting guide to said condyles while resecting the distal ends of the medial and lateral condyles.

16. A method as claimed in claim 12, wherein said plane, which is parallel to said prospective planar resection and from which the thickness to be resected is determined, is tangent to one of said condyles.

17. A method as claimed in claim 12, comprising securing two pins in said condyles in accordance with the angular or rotational position established by said tool to serve as a datum, said pins holding the tool in said angular or rotational position, mounting a cutting guide on the tool while the tool remains angularly secured on said pins, using said cutting guide to resect the distal planar resection on the condyles, removing the tool from the pins, mounting a second cutting guide on said pins and using said second cutting guide to obtain the resections at the posterior and anterior surfaces.

18. A method as claimed in claim 17, comprising providing a caliper on said tool and rotating said caliper with said tool around an axis located in said tangential plane through an angle equal to said determined angle when said rod is rotated.

19. A method as claimed in claim 17, comprising securing said cutting guide to said condyles while resecting the distal ends of the medial and lateral condyles.

20. A tool for enabling resections to be made on the medial and lateral femoral condyles of a knee for installation of a femoral prosthesis, said tool comprising
    means for engaging an intramedullary rod in a femur to rotate said tool on said rod through an angle to a determined angular or rotational position about plus or minus 15° relative to a plane tangent to posterior surfaces of the medial and lateral condyles,
    means for measuring a distance between an anterior femoral cortex surface and a plane inclined, with respect to the plane tangent to the posterior surfaces of the medial and lateral condyles about an axis located in said plane, at an angle equal to the angle of rotation of said tool on said rod when moved to said determined angular or rotational position, and
    means for mounting a guide on the tool while the tool remains engaged on the intramedullary rod, said guide having guide slots to pass a resector to produce an anterior or distal resection on the condyles.

21. A tool as claimed in claim 20, wherein said means for measuring distance between the anterior femoral cortex surface and said plane inclined with respect to the plane tangent to the posterior surfaces of the medial and lateral femoral condyles comprises a caliper.

22. A tool as claimed in claim 21, wherein said means for engaging said rod comprises a rotatable sleeve, said tool further comprising means providing slidable movement in at least two directions between said sleeve and said caliper.

23. A tool as claimed in claim 22, comprising a scale on said caliper for indicating prosthesis size based on said distance measured between the anterior femoral cortex surface and said plane inclined with respect to the plane tangent to the posterior surfaces of the medial and lateral femoral condyles, said scale for also indicating differences between the measured distance and a prosthetic size.

24. A tool as claimed in claim 22, comprising an angle scale to indicate the angle of rotation of said sleeve.

25. A tool as claimed in claim 20, wherein said means for mounting a guide comprises a scale for indicating the distance of said guide slots from a plane at which the tool abuts against distal ends of the condyles.

26. A tool as claimed in claim 20, comprising means on said guide for securing said guide to said condyles while the anterior or distal resection on the condyles is being made.

27. A tool mountable on an intramedullary rod loosely mounted in a femur to rotate the rod and tool and to measure an anterior-posterior dimension taking into account the rotation and angulation of the tool, said tool comprising:
    an engaging device for engaging an intramedullary rod loosely mounted in a femur having an anterior femoral cortex to rotate said tool therewith,
    an anterior feeler for contacting the anterior cortex surface of the femur,
    a posterior feeler or feelers for contacting posterior surfaces of medial and lateral condyles to establish a plane tangent to said posterior surfaces,
    a caliper for measuring the distance between the anterior femoral cortex and the posterior femoral condyles, said caliper being operatively engaged to said engaging device and to said anterior and posterior feelers,
    a pivot between said caliper and said posterior feeler for providing relative pivotable movement therebetween about an axis disposed in said tangent plane, and
    means providing relative movement between said pivot and said engaging means to permit said tool to be rotated on said rod at least about plus or minus 15° and said caliper to be rotated around said pivot so that the caliper is positioned to measure an anterior-posterior dimension represented by a distance from said anterior cortex surface to said tangent plane which is inclined at an angle equal to said angle at which the tool and caliper have been rotated.

28. A tool as claimed in claim 27, wherein said engaging device comprises a rotatable sleeve, said means providing relative movement between the pivot and the engaging means comprises a slidable connection between said rotatable sleeve and said caliper.

29. A tool as claimed in claim 27, comprising a scale on said caliper for indicating prosthesis size based on said distance measured between the anterior femoral cortex surface and said tangent plane, said scale for also indicating differences between the measured distance and a prosthetic size.

30. A method for forming planar resections on the medial and lateral condyles of a femur of a knee to form seating surfaces to receive a femoral prosthesis to properly articulate with a tibial and patellar prosthesis, said method comprising:
    measuring the thicknesses which will be resected by a prospective planar resection to be made at the posterior of the medial and lateral condyles of a femur at which a distance between an anterior surface of the femoral cortex and the prospective planar resection is substantially equal to an interior dimension of a femoral prosthesis to be fitted on said femur, said planar resection producing resection of the medial and lateral condyles at said posterior surface of respective thicknesses which are not necessarily equal, resecting a distal end of the medial and lateral condyles along a plane which produces respective resected thicknesses, not necessarily equal, at said medial and lateral condyles and wherein the distal medial resection is usually substantially equal to the measured posterior medial condyle thickness to be resected and the distal lateral resection is usually substantially equal to the measured posterior lateral condyle thickness to be resected, and resecting the medial and lateral condyles along a plane at the anterior surfaces thereof substantially flush with the anterior surface of the femoral cortex, and along said prospective planar resection.

31. A method for forming planar resections on the medial and lateral condyles of a femur of a knee to form seating surfaces to receive a femoral prosthesis to properly articulate with a tibial and patellar prosthesis, said method comprising:

measuring the thicknesses which will be resected by a prospective planar resection to be made at the posterior of the medial and lateral condyles of a femur at which a distance between an anterior surface of the femoral cortex and the prospective planar resection is substantially equal to an interior dimension of a femoral prosthesis to be fitted on said femur, said planar resection producing resection of the medial and lateral condyles at said posterior surface of respective thicknesses which are not necessarily equal, resecting the medial and lateral condyles along a plane at the anterior surfaces thereof substantially flush with the anterior surface of the femoral cortex, resecting a distal end of the medial and lateral condyles along a plane which produces respective resected thicknesses, not necessarily equal, at said medial and lateral condyles and wherein the distal medial resection is substantially equal to the measured posterior medial condyle thickness to be resected and the distal lateral resection is substantially equal to the measured posterior lateral condyle thickness to be resected, and resecting the medial and lateral condyles along said measured prospective planar resection.

32. A method as claimed in claim 2, wherein the angular or rotational position of said prospective planar resection is substantially parallel to the tibial prosthesis in the medio lateral plane.

33. A method as claimed in claim 2, wherein the angular or rotational position of said prospective planar resection is substantially parallel to a prospective tibial resection.

34. A method as claimed in claim 2, wherein the angular or rotational position of said prospective planar resection places the femoral prosthesis in a proper rotational and angular alignment on the distal femur to reconstruct a normal and stable patellofemoral joint anteriorly and properly articulates the femoral prosthesis posteriorly and distally with a prospective tibial prosthesis.

35. A method for forming planar resections on the medial and lateral condyles of a femur to form seating surfaces to receive a femoral prosthesis and to properly articulate with a tibial and patellar prosthesis, said method comprising:

measuring for the size of the femoral prosthesis to be received by determining a first distance between an anterior surface of the femoral cortex and a plane tangent to a posterior surface of the medial and lateral condyles of a femur;

using a graduated scale to compare the first distance to at least two standard femoral prosthesis sizes;

measuring a second distance between the first distance and the size of a larger standard femoral prosthesis size;

measuring a thickness or thicknesses to be resected at the posterior surface of the medial and lateral condyles of the femur, the thickness being equal to the difference between the thickness of the posterior condyles of the larger standard femoral prosthesis and the second distance;

resecting the medial and lateral condyles along a plane at the anterior surfaces thereof substantially flush with the anterior surface of the femoral cortex; and resecting distal ends of the medial and lateral condyles along a plane which produces respective resected thicknesses at said medial and lateral condyles, not necessarily equal, wherein the distal medial resection is substantially equal to the measured posterior medial condyle thickness and the distal lateral resection is substantially equal to the measured posterior lateral condyle thickness.

36. An apparatus for forming planar resections on the medial and lateral condyles of a femur to form seating surfaces to receive a femoral prosthesis and to properly articulate with a tibial and patellar prosthesis, said apparatus comprising:

a caliper feeler and measurement plate to measure for the size of the femoral prosthesis to be received, said caliper feeler and measurement plate adapted to determine a first distance between an anterior surface of the femoral cortex and a plane tangent to a posterior surface of the medial and lateral condyles of a femur, the caliper feeler referencing the anterior surface of the femoral cortex and the measurement plate referencing the plane tangent to the posterior surface of the medial and lateral condyles;

a graduated scale to compare the first distance to at least two standard femoral prosthesis sizes and to determine the smaller of the at least two standard femoral prosthesis sizes;

a graduated scale to measure a second distance between the first distance and the size of the smaller standard femoral prosthesis size, so that a thickness or thicknesses can be measured to be resected at the posterior surface of the medial and lateral condyles of the femur by adding the thickness of the posterior condyles of the smaller standard femoral prosthesis and the second distance;

a tool to resect the medial and lateral condyles along a plane at the anterior surfaces thereof flush with the anterior surface of the femoral cortex; and a tool to resect distal ends of the medial and lateral condyles along a plane which produces respective resected thicknesses at said medial and lateral condyles, not necessarily equal, wherein the distal medial resection is substantially equal to the measured posterior medial condyle thickness and the distal lateral resection is substantially equal to the measured posterior lateral condyle thickness.

37. An apparatus as claimed in claim 36, including a tool to resect the measured thickness at the posterior surface of the medial and lateral condyles of the femur.

38. An apparatus as claimed in claim 36, including a longitudinal rod to be engaged in the femur such that an end of the rod projects from the femur.

39. An apparatus as claimed in claim 38, including a tool to be mounted on the projecting end of the rod to establish, by said tool, an angular or rotational position of said resection at the posterior surface of the medial and lateral condyles at a determined angle with respect to a tangential plane at the posterior surfaces of the medial and lateral condyles.

40. An apparatus as claimed in claim 39, wherein said tool establishes that the angular or rotational position of said resection at the posterior surface of the medial and lateral condyles is substantially parallel to the floor.

41. An apparatus as claimed in claim 39, wherein said tool establishes that the angular or rotational position of said resection at the posterior surface of the medial and lateral condyles is substantially parallel to a prospective tibial resection.

42. An apparatus as claimed in claim 39, wherein the angular or rotational position of said resection at the posterior surface of the medial and lateral condyles places the femoral prosthesis in a proper rotational and angular alignment on the distal femur to reconstruct a normal and stable patellofemoral joint anteriorly and properly articulates the femoral prosthesis posteriorly and distally with a prospective tibial prosthesis.

43. An apparatus as claimed in claim 39, wherein the determined angle is about plus or minus 15 degrees.

44. An apparatus as claimed in claim 43, wherein the determined angle is about 3 degrees.

45. A method for forming planar resections on the medial and lateral condyles of a femur to form seating surfaces to receive a femoral prosthesis and to properly articulate with a tibial and patellar prosthesis, said method comprising:

measuring for the size of the femoral prosthesis to be received by determining a first distance between an anterior surface of the femoral cortex and a plane tangent to a posterior surface of the medial and lateral condyles of a femur;

using a graduated scale to compare the first distance to at least two standard femoral prosthesis sizes;

measuring a second distance between the first distance and the size of the smaller standard femoral prosthesis size;

measuring a thickness or thicknesses to be resected at the posterior surface of the medial and lateral condyles of the femur, the thickness being equal to the thickness of the posterior condyles of the smaller standard femoral prosthesis plus the second distance; and measuring a thickness or thicknesses to be resected at the distal ends of the medial and lateral condyles, the thickness being equal to the thickness of the distal surface of the smaller standard femoral prosthesis plus the second distance.

46. A method as claimed in claim 45, further comprising the steps or resecting the distal ends of the medial and lateral condyles along a plane which produces respective resected thicknesses at said medial and lateral condyles, not necessarily equal, and resecting the measured thickness at the posterior surface of the medial and lateral condyles.

47. A method as claimed in claim 45, further comprising the step of resecting the medial and lateral condyles along a plane at the anterior surfaces thereof substantially flush with the anterior surface of the femoral cortex.

48. A method as claimed in claim 45, further comprising the step of choosing a standard prosthesis size that is smaller than the smaller of the two standard femoral prosthesis sizes.

49. A method for forming planar resections on the medial and lateral condyles of a femur to form seating surfaces to receive a femoral prosthesis and to properly articulate with a tibial and patellar prosthesis, said method comprising:

measuring for the size of the femoral prosthesis to be received by determining a first distance between an anterior surface of the femoral cortex and a plane tangent to a posterior surface of the medial and lateral condyles of a femur;

using a graduated scale to compare the first distance to at least two standard femoral prosthesis sizes;

measuring a second distance between the first distance and the size of the larger standard femoral prosthesis size;

measuring a thickness or thicknesses to be resected at the posterior surface of the medial and lateral condyles of the femur, the thickness being equal to the difference between the thickness of the posterior condyles of the larger standard femoral prosthesis and the second distance;

resecting the medial and lateral condyles along a plane at the anterior surfaces thereof substantially flush with the anterior surface of the femoral cortex; and measuring a thickness or thicknesses to be resected at the distal ends of the medial and lateral condyles, the thickness being equal to the difference between the thickness of the distal surface of the larger standard femoral prosthesis and the second distance.

\* \* \* \* \*